US010329587B2

(12) United States Patent
Church et al.

(10) Patent No.: US 10,329,587 B2
(45) Date of Patent: Jun. 25, 2019

(54) ORTHOGONAL CAS9 PROTEINS FOR RNA-GUIDED GENE REGULATION AND EDITING

(71) Applicant: President and Fellows of Harvard College, Cambridge, MA (US)

(72) Inventors: George M. Church, Brookline, MA (US); Kevin M. Esvelt, Auburndale, MA (US); Prashant G. Mali, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/903,728

(22) PCT Filed: Jul. 8, 2014

(86) PCT No.: PCT/US2014/045700
§ 371 (c)(1),
(2) Date: Jan. 8, 2016

(87) PCT Pub. No.: WO2015/006294
PCT Pub. Date: Jan. 15, 2015

(65) Prior Publication Data
US 2016/0222416 A1    Aug. 4, 2016

Related U.S. Application Data

(60) Provisional application No. 61/844,844, filed on Jul. 10, 2013.

(51) Int. Cl.
*C12N 15/113*    (2010.01)
*C12N 9/22*    (2006.01)
*C12N 15/90*    (2006.01)
*C12N 15/85*    (2006.01)
*C07K 2/00*    (2006.01)
*C12N 15/11*    (2006.01)

(52) U.S. Cl.
CPC ............. *C12N 15/907* (2013.01); *C07K 2/00* (2013.01); *C12N 9/22* (2013.01); *C12N 15/11* (2013.01); *C12N 15/113* (2013.01); *C12N 15/85* (2013.01); *C12N 2310/3519* (2013.01); *C12N 2320/33* (2013.01); *C12N 2320/50* (2013.01); *C12N 2800/107* (2013.01); *C12N 2800/40* (2013.01); *C12N 2800/80* (2013.01); *C12N 2810/10* (2013.01); *C12N 2830/00* (2013.01); *C12N 2830/34* (2013.01); *C12N 2999/007* (2013.01); *C12Y 301/00* (2013.01)

(58) Field of Classification Search
None
See application file for complete search history.

(56) References Cited

U.S. PATENT DOCUMENTS

| 6,586,240 B1 | 7/2003 | Singer et al. |
| 8,697,359 B1 | 4/2014 | Zhang |
| 2010/0076057 A1 | 3/2010 | Sontheimer et al. |
| 2011/0189776 A1 | 8/2011 | Terns et al. |
| 2011/0223638 A1 | 9/2011 | Wiedenheft et al. |
| 2011/0301073 A1 | 12/2011 | Gregory et al. |
| 2013/0130248 A1 | 5/2013 | Haurwitz et al. |
| 2013/0253040 A1 | 9/2013 | Miller et al. |
| 2014/0068797 A1 | 3/2014 | Doudna et al. |
| 2014/0179770 A1* | 6/2014 | Zhang .................... C12N 15/86 514/44 R |

FOREIGN PATENT DOCUMENTS

| WO | 2008/108989 A2 | 9/2008 |
| WO | 2010/054108 A2 | 5/2010 |
| WO | 2011/143124 A2 | 11/2011 |
| WO | 2012/164565 A1 | 12/2012 |
| WO | 2013/098244 A1 | 7/2013 |
| WO | 2013/126794 A1 | 8/2013 |
| WO | 2013/141680 A1 | 9/2013 |
| WO | 2013/142578 A1 | 9/2013 |
| WO | 2013/176772 A1 | 11/2013 |
| WO | 2014/022702 A2 | 2/2014 |
| WO | 2014/093635 A1 | 6/2014 |

OTHER PUBLICATIONS

International Search Report issued from corresponding PCT/US2014/045700, dated Nov. 17, 2014.
Cong, L et al. Multiplex Genome Engineering Using CRISPR/Cas Systems. Science. Feb. 15, 2013; vol. 339, No. 6121, pp. 819-823; p. 820, center column, second paragraph to right column, first paragraph; Figure 2. doi: 10.1126/science.123114.
Mali, P etal. RNA-Guided Human Genome Engineering Via Cas9. Science. Feb. 15, 2013; vol. 339, No. 6121, pp. 823-826; abstract; p. 823, middle column, second paragraph to right column, second paragraph; Figures 1, 2. doi: 1 0.1126/science.123203.
Zhang, F et al. Nature Biotechnology. Feb. 2011. vol. 29, No. 2, pp. 149-153; p. 150, figure 1C and 10. doi: 10.1038/nbt.177.
Al-Attar et al., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.
Carroll, "A CRISPR Approach to Gene Targeting" 20(9) Molecular Therapy 1658-1660 (Sep. 2012).
Cong, Le et al. Multiplex Genome Engineering Using CRISPR/Cas Systems. Science. Feb. 15, 2013; vol. 339, No. 6121, pp. 819-823; p. 820, center column, second paragraph to right column, first paragraph; Figure 2. doi: 10.1126/science.123114.

(Continued)

*Primary Examiner* — Catherine S Hibbert
(74) *Attorney, Agent, or Firm* — Banner & Witcoff, Ltd.

(57) ABSTRACT

Methods of modulating expression of a target nucleic acid in a cell are provided including use of multiple orthogonal Cas9 proteins to simultaneously and independently regulate corresponding genes or simultaneously and independently edit corresponding genes.

17 Claims, 17 Drawing Sheets
Specification includes a Sequence Listing.

(56) References Cited

OTHER PUBLICATIONS

Dueber, John E, et al., "Synthetic protein scaffolds provide modular control over metabolic flux," Nature Biotechnology, Gale Group Inc, US, vol. 27, No. 8, Aug. 1, 2009 (Aug. 1, 2009), pp. 753-750.
Flanagan, Lisa A., et al. "Filamin A, the Arp2/3 complex, and the morphology and function of cortical actin filaments in human melanoma cells", The Journal of Cell Biology : JCB, The Rockefeller University Press, US, vol. 155, No. 4 Nov. 12, 2001 (Nov. 12, 2001), pp. 511-517.
Gasiunas, G et al Cas9-crRNA Ribonucleoprotein Complex Mediates Specific DNA Cleavage for Adaptive Immunity in Bacteria. PNAS. Sep. 4, 2012. vol. 109, No. 39; pp. E2579-E2586; p. E2583, first column, first paragraph. DOI: 1 0.1073/pnas.1208507109.
Gilbert, et al. "CRISPR-Mediated Modular RNA-Guided Regulation of Transcription in Eukaryotes", Cell, Jul. 18, 2013. vol. 154 No. 2, pp. 442-451, Elsevier, Inc.
Hale et al., Essential Features and Rational Design of CRISPR RNAs That Function With the Cas RAMP Module Complex to Cleave RNAs, Molecular Cell, (20 12) vol. 45, Issue 3, 292-302.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
International Search Report issued in corresponding PCT/US2013/075317, dated Apr. 15, 2014.
International Search Report issued in corresponding PCT/US2013/075326, dated Aug. 22, 2014.
Jinek , et al. 'RNA-programmed genome editing in human cells.' eLite 2013;2:e00471 . [retrieved 1-3, 6, 7, 10-12 on Jun. 3, 2014). Retrieved from the Internet. <URL: http://elife .elifesciences.org/content/2/e00471 >. entire document.
Jinek, M et al. A Programmable Dual-RNA-Guided DNA Endonuclease in Adaptive Bacterial Immunity. Science. Jun. 28, 2012. vol. 337; pp. 816-821; DOI: 10.1126/science.1225829.
Makarova et al., "Evolution and classification of the CRISPR-Cas systems" 9(6) Nature Reviews Microbiology 467-477 (1-23) (Jun. 2011).
Qi, L et al. Repurposing CRISPR as an RNA-guided platform for sequence-specific control of gene expression. Cell. Feb. 28, 2013; vol. 152, No. 5, pp. 1173-1183; p. 1175, right column, fourth paragraph to p. 1177, left column, first paragraph; Figures 2, 4. doi: 10.1 016/j.cell.2013.02.022.
Rho, Mina et al. 'Diverse CRISPRs Evolving in Human Microbiomes.' PLoS Genetics. vol. 8, No. 6. 1-14 pp. 1-12. Jun. 2012. entire document.
Sontheimer Erik, Project 7: Establishing RNA-Directed DNA Targeting in Eukaryotic Cells; Project dates: Nov. 16, 2011 to Dec. 31, 2012 (Feb. 4, 2012).
Tam, James P., et al., "Orthogonal ligation strategies for peptide and protein", Biopolymers, John Wiley & Sons, Inc, US, vol. 51, No. 5, Jan. 1, 1999 (Jan. 1, 1999), pp. 311-332.
Wiedenheft eta!., "RNA-guided genetic silencing systems in bacteria and archaea" 482 Nature 331-338 (Feb. 16, 2012).
Cong, Le et al. "Multiplex Genome Engineering Using CRISPR/CAS Systems". Science. Feb. 15, 2013; vol. 339, No. 6121, pp. 819-823; p. 820, center column, second paragraph to right column, first paragraph; Figure 2 doi: 10.112/science.123114 and Supplementary Materials, Jan. 3, 2013, Science Express DOI: 10/1126/science.1231143.
Zhang, Yan et al. "Processing-Independent CRISPR RNAs Limit Natural Transformation in Neisseria meningitidis" Molecular Cell, vol. 50 (May 23, 2013), pp. 488-503.

* cited by examiner

SEQUENCE LISTING

```
<160> NUMBER OF SEQ ID NOS: 39

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
```

```
                165                 170                 175
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590
```

-continued

```
Thr Tyr His Asp Leu Leu Lys Ile Ile Lys Asp Lys Asp Phe Leu Asp
    595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
    675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
    755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
    995                 1000                1005
```

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gtcccctcca ccccacagtg ggg                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggggccacta gggacaggat tgg                                              23

<210> SEQ ID NO 4
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
taatactttt atctgtcccc tccacccac agtggggcca ctagggacag gattggtgac      60
agaaaagccc c                                                          71

<210> SEQ ID NO 5
<211> LENGTH: 100
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ggggccacta gggacaggat guuuagagc uagaaauagc aaguuaaaau aaggcuaguc      60
cguuaucaac uugaaaaagu ggcaccgagu cggugcuuuu                          100

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcccctcca ccccacagtg crr                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtcccctcca ccccacagtg cag                                              23

```
<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtcccctcca ccccacagtg caa                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtcccctcca ccccacagtg cgg                                              23

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgtcccctcc accccacagt ggggccacta gggacaggat tggtgacaga aa              52

<210> SEQ ID NO 11
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 tgtcccccccc accccacagt ggggccacta gggacaggat tggtgacaga aa             52

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaccctcc accccacagt ggggccacta gggacaggat tggtgacaga aa              52

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 tgtccccctcc tttttcagt ggggccacta gggacaggat tggtgacaga aa              52

<210> SEQ ID NO 14
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tctgtcacca atcctgtc                                                      18

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgtcaccaat cctg                                                          14

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcaccaatcc                                                               10

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
caccggggtg gtgcccatcc tgg                                                23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggtgcccatc ctggtcgagc tgg                                                23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cccatcctgg tcgagctgga cgg                                                23

<210> SEQ ID NO 20
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggccacaagt tcagcgtgtc cgg                                             23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cgcaaataag agctcaccta cgg                                             23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ctgaagttca tctgcaccac cgg                                             23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccggcaagct gcccgtgccc tgg                                             23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gaccaggatg ggcaccaccc cgg                                             23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gccgtccagc tcgaccagga tgg                                             23

<210> SEQ ID NO 26
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 26
ggccggacac gctgaacttg tgg                                            23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taacagggta atgtcgaggc cgg                                            23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aggtgagctc ttatttgcgt agg                                            23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cttcagggtc agcttgccgt agg                                            23

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gggcacgggc agcttgccgg tgg                                            23

<210> SEQ ID NO 31
<211> LENGTH: 36
<212> TYPE: RNA
<213> ORGANISM: Streptococcus pyogenes

<400> SEQUENCE: 31
guuuuagagc uaugcuguuu ugaauggucc caaaac                              36

<210> SEQ ID NO 32
<211> LENGTH: 36
<212> TYPE: RNA
<213> ORGANISM: Streptococcus thermophilus

<400> SEQUENCE: 32
```

```
guuuuuguac ucucaagauu uaaguaacug uacaac                               36
```

<210> SEQ ID NO 33
<211> LENGTH: 36
<212> TYPE: RNA
<213> ORGANISM: Neisseria meningitidis

<400> SEQUENCE: 33

```
guuguagcuc ccuuucucau uucgcagugc uacaau                               36
```

<210> SEQ ID NO 34
<211> LENGTH: 36
<212> TYPE: RNA
<213> ORGANISM: Treponema denticola

<400> SEQUENCE: 34

```
guuugagagu uguguaauuu aagauggauc ucaaac                               36
```

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

```
taccatctca agcttgttga                                                 20
```

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

```
actttaaaag tattcgccat                                                 20
```

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
gtcccctcca ccccacagtg cgggaaa                                         27
```

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
gtcccctcca ccccacagtg caagaaa                                         27
```

<210> SEQ ID NO 39
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 39
gtcccctcca ccccacagtg ggaggatt                                              28
```

US 10,329,587 B2

ORTHOGONAL CAS9 PROTEINS FOR RNA-GUIDED GENE REGULATION AND EDITING

RELATED APPLICATION DATA

This application is a National Stage Application under 35 U.S.C. 371 of co-pending PCT application PCT/US2014/045700 designating the United States and filed Jul. 8, 2014, which claims the benefit of U.S. Provisional Patent Application No. 61/844,844 filed on Jul. 10, 2013 each of which are hereby incorporated by reference in their entireties.

STATEMENT OF GOVERNMENT INTERESTS

This invention was made with government support under Grant No. P50 HG005550 from the National Institutes of health and DE-FG02-02ER63445 from the Department of Energy. The government has certain rights in the invention.

SEQUENCE LISTING

The instant application contains a Sequence Listing which has been submitted electronically in ASCII format and is hereby incorporated by reference in its entirety. Said ASCII copy, created on Jun. 21, 2017, is named 010498_00706-US_SL.txt and is 21,076 bytes in size.

BACKGROUND

Bacterial and archaeal CRISPR-Cas systems rely on short guide RNAs in complex with Cas proteins to direct degradation of complementary sequences present within invading foreign nucleic acid. See Deltcheva, E. et al. CRISPR RNA maturation by trans-encoded small RNA and host factor RNase III. *Nature* 471, 602-607 (2011); Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012); Jinek, M. et al. A programmable dual-RNA-guided DNA endonuclease in adaptive bacterial immunity. *Science* 337, 816-821 (2012); Sapranauskas, R. et al. The *Streptococcus thermophilus* CRISPR/Cas system provides immunity in *Escherichia coli*. *Nucleic acids research* 39, 9275-9282 (2011); and Bhaya, D., Davison, M. & Barrangou, R. CRISPR-Cas systems in bacteria and archaea: versatile small RNAs for adaptive defense and regulation. *Annual review of genetics* 45, 273-297 (2011). A recent in vitro reconstitution of the *S. pyogenes* type II CRISPR system demonstrated that crRNA ("CRISPR RNA") fused to a normally trans-encoded tracrRNA ("trans-activating CRISPR RNA") is sufficient to direct Cas9 protein to sequence-specifically cleave target DNA sequences matching the crRNA. Expressing a gRNA homologous to a target site results in Cas9 recruitment and degradation of the target DNA. See H. Deveau et al., Phage response to CRISPR-encoded resistance in *Streptococcus thermophilus*. *Journal of Bacteriology* 190, 1390 (February, 2008).

SUMMARY

Aspects of the present disclosure are directed to a complex of a guide RNA, a DNA binding protein and a double stranded DNA target sequence. According to certain aspects, DNA binding proteins within the scope of the present disclosure include a protein that forms a complex with the guide RNA and with the guide RNA guiding the complex to a double stranded DNA sequence wherein the complex binds to the DNA sequence. This aspect of the present disclosure may be referred to as co-localization of the RNA and DNA binding protein to or with the double stranded DNA. In this manner, a DNA binding protein-guide RNA complex may be used to localize a transcriptional regulator protein or domain at target DNA so as to regulate expression of target DNA. According to one aspect, two or more or a plurality of orthogonal RNA guided DNA binding proteins or a set of orthogonal RNA guided DNA binding proteins, may be used to simultaneously and independently regulate genes in DNA in a cell. According to one aspect, two or more or a plurality of orthogonal RNA guided DNA binding proteins or a set of orthogonal RNA guided DNA binding proteins, may be used to simultaneously and independently edit genes in DNA in a cell. It is to be understood that where reference is made to a DNA binding protein or an RNA guided DNA binding proteins, such reference includes an orthogonal DNA binding protein or an orthogonal RNA guided DNA binding protein. Such orthogonal DNA binding proteins or orthogonal RNA guided DNA binding proteins may have nuclease activity, they may have nickase activity or they may be nuclease null.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding a RNA guided nuclease-null DNA binding protein, that binds to the DNA and is guided by the one or more RNAs, introducing into the cell a third foreign nucleic acid encoding a transcriptional regulator protein or domain, wherein the one or more RNAs, the RNA guided nuclease-null DNA binding protein, and the transcriptional regulator protein or domain are expressed, wherein the one or more RNAs, the RNA guided nuclease-null DNA binding protein and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein further encodes the transcriptional regulator protein or domain fused to the RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition. According to one aspect, the transcriptional regulator protein or domain is a transcriptional repressor. According to one aspect, the transcriptional regulator protein or domain downregulates expression of the target nucleic acid. According to one aspect, the transcriptional regulator protein or domain downregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding a RNA guided nuclease-null DNA binding proteins of a Type II CRISPR System, that binds to the DNA and is guided by the one or more RNAs, introducing into the cell a third foreign nucleic acid encoding a transcriptional regulator protein or domain, wherein the one or more RNAs, the RNA guided nuclease-null DNA binding protein of a Type II CRISPR System, and the transcriptional regulator protein or domain are expressed, wherein the one or more RNAs, the RNA guided nuclease-null DNA binding protein of a Type II CRISPR System and the transcriptional regulator protein or domain co-localize to the DNA and wherein the transcriptional regulator protein or domain regulates expression of the target nucleic acid.

According to one aspect, the foreign nucleic acid encoding an RNA guided nuclease-null DNA binding protein of a Type II CRISPR System further encodes the transcriptional regulator protein or domain fused to the RNA guided nuclease-null DNA binding protein of a Type II CRISPR System. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, a method of modulating expression of a target nucleic acid in a cell is provided including introducing into the cell a first foreign nucleic acid encoding one or more RNAs (ribonucleic acids) complementary to DNA (deoxyribonucleic acid), wherein the DNA includes the target nucleic acid, introducing into the cell a second foreign nucleic acid encoding a nuclease-null Cas9 protein that binds to the DNA and is guided by the one or more RNAs, introducing into the cell a third foreign nucleic acid encoding a transcriptional regulator protein or domain, wherein the one or more RNAs, the nuclease-null Cas9 protein, and the transcriptional regulator protein or domain are expressed, wherein the one or more RNAs, the nuclease-null Cas9 protein and the transcriptional regulator protein or domain co-localize to the DNA and wherein the transcriptional regulator protein or domain regulates expression of the target nucleic acid.

According to one aspect, the foreign nucleic acid encoding a nuclease-null Cas9 protein further encodes the transcriptional regulator protein or domain fused to the nuclease-null Cas9 protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to one aspect a cell is provided that includes a first foreign nucleic acid encoding one or more RNAs complementary to DNA, wherein the DNA includes a target nucleic acid, a second foreign nucleic acid encoding an RNA guided nuclease-null DNA binding protein, and a third foreign nucleic acid encoding a transcriptional regulator protein or domain wherein the one or more RNAs, the RNA guided nuclease-null DNA binding protein and the transcriptional regulator protein or domain are members of a co-localization complex for the target nucleic acid.

According to one aspect, the foreign nucleic acid encoding an RNA guided nuclease-null DNA binding protein further encodes the transcriptional regulator protein or domain fused to an RNA guided nuclease-null DNA binding protein. According to one aspect, the foreign nucleic acid encoding one or more RNAs further encodes a target of an RNA-binding domain and the foreign nucleic acid encoding the transcriptional regulator protein or domain further encodes an RNA-binding domain fused to the transcriptional regulator protein or domain.

According to one aspect, the cell is a eukaryotic cell. According to one aspect, the cell is a yeast cell, a plant cell or an animal cell. According to one aspect, the cell is a mammalian cell.

According to one aspect, the RNA is between about 10 to about 500 nucleotides. According to one aspect, the RNA is between about 20 to about 100 nucleotides.

According to one aspect, the transcriptional regulator protein or domain is a transcriptional activator. According to one aspect, the transcriptional regulator protein or domain upregulates expression of the target nucleic acid. According to one aspect, the transcriptional regulator protein or domain upregulates expression of the target nucleic acid to treat a disease or detrimental condition. According to one aspect, the target nucleic acid is associated with a disease or detrimental condition.

According to one aspect, the one or more RNAs is a guide RNA. According to one aspect, the one or more RNAs is a tracrRNA-crRNA fusion.

According to one aspect, the DNA is genomic DNA, mitochondrial DNA, viral DNA, or exogenous DNA.

According to certain aspects, the RNA guided nuclease-null DNA binding protein is an RNA guided nuclease-null DNA binding protein of a Type II CRISPR System. According to certain aspects, the RNA guided nuclease-null DNA binding protein is a nuclease-null Cas9 protein.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase, which may be an orthogonal RNA guided DNA binding protein nickase, and being guided by the two or more RNAs, wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR System and being guided by the two or more RNAs, wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks.

According to one aspect, a method of altering a DNA target nucleic acid in a cell is provided that includes introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks.

According to the methods of altering a DNA target nucleic acid, the two or more adjacent nicks are on the same strand of the double stranded DNA. According to one aspect, the two or more adjacent nicks are on the same strand of the double stranded DNA and result in homologous recombination. According to one aspect, the two or more adjacent nicks are on different strands of the double stranded DNA. According to one aspect, the two or more adjacent nicks are on different strands of the double stranded DNA and create double stranded breaks. According to one aspect, the two or more adjacent nicks are on different strands of the double stranded DNA and create double stranded breaks resulting in nonhomologous end joining. According to one aspect, the two or more adjacent nicks are on different strands of the double stranded DNA and are offset with respect to one another. According to one aspect, the two or more adjacent nicks are on different strands of the double stranded DNA and are offset with respect to one another and create double stranded breaks. According to one aspect, the two or more adjacent nicks are on different strands of the double stranded DNA and are offset with respect to one another and create double stranded breaks resulting in nonhomologous end joining. According to one aspect, the method further includes introducing into the cell a third foreign nucleic acid encoding a donor nucleic acid sequence wherein the two or more nicks results in homologous recombination of the target nucleic acid with the donor nucleic acid sequence.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase and being guided by the two or more RNAs, and wherein the two or more RNAs and the at least one RNA guided DNA binding protein nickase are expressed and wherein the at least one RNA guided DNA binding protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one RNA guided DNA binding protein nickase of a Type II CRISPR system and being guided by the two or more RNAs, and wherein the two or more RNAs and the at least one RNA guided DNA binding protein nickase of a Type II CRISPR System are expressed and wherein the at least one RNA guided DNA binding protein nickase of a Type II CRISPR System co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a method of altering a DNA target nucleic acid in a cell is provided including introducing into the cell a first foreign nucleic acid encoding two or more RNAs with each RNA being complementary to an adjacent site in the DNA target nucleic acid, introducing into the cell a second foreign nucleic acid encoding at least one Cas9 protein nickase having one inactive nuclease domain and being guided by the two or more RNAs, and wherein the two or more RNAs and the at least one Cas9 protein nickase are expressed and wherein the at least one Cas9 protein nickase co-localizes with the two or more RNAs to the DNA target nucleic acid and nicks the DNA target nucleic acid resulting in two or more adjacent nicks, and wherein the two or more adjacent nicks are on different strands of the double stranded DNA and create double stranded breaks resulting in fragmentation of the target nucleic acid thereby preventing expression of the target nucleic acid.

According to one aspect, a cell is provided including a first foreign nucleic acid encoding two or more RNAs with each RNA being complementary to an adjacent site in a DNA target nucleic acid, and a second foreign nucleic acid encoding at least one RNA guided DNA binding protein nickase, and wherein the two or more RNAs and the at least one RNA guided DNA binding protein nickase are members of a co-localization complex for the DNA target nucleic acid.

According to one aspect, the RNA guided DNA binding protein nickase is an RNA guided DNA binding protein nickase of a Type II CRISPR System. According to one aspect, the RNA guided DNA binding protein nickase is a Cas9 protein nickase having one inactive nuclease domain.

According to one aspect, the cell is a eukaryotic cell. According to one aspect, the cell is a yeast cell, a plant cell or an animal cell. According to one aspect, the cell is a mammalian cell.

According to one aspect, the RNA includes between about 10 to about 500 nucleotides. According to one aspect, the RNA includes between about 20 to about 100 nucleotides.

According to one aspect, the target nucleic acid is associated with a disease or detrimental condition.

According to one aspect, the two or more RNAs are guide RNAs. According to one aspect, the two or more RNAs are tracrRNA-crRNA fusions.

According to one aspect, the DNA target nucleic acid_is genomic DNA, mitochondrial DNA, viral DNA, or exogenous DNA.

According to one aspect, methods may include the simultaneous use of orthogonal RNA guided DNA binding protein nickases, orthogonal RNA guided DNA binding protein nucleases, orthogonal RNA guided nuclease null DNA binding proteins. Accordingly, in the same cell, alterations created by nicking or cutting the DNA and translational mediation can be carried out. Further, one or more or a plurality of exogenous donor nucleic acids may also be added to a cell using methods known to those of skill in the art of introducing nucleic acids into cells, such as electroporation, and the one or more or a plurality of exogenous donor nucleic acids may be introduced into the DNA of the cell by recombination, such as homologous recombination, or other mechanisms known to those of skill in the art. Accordingly, the use of a plurality of orthogonal RNA guided DNA binding proteins described herein allows a single cell to be altered by nicking or cutting, allows donor nucleic acids to be introduced into the DNA in the cell and allows genes to be transcriptionally regulated.

Further features and advantages of certain embodiments of the present invention will become more fully apparent in the following description of embodiments and drawings thereof, and from the claims.

BRIEF DESCRIPTION OF THE DRAWINGS

The foregoing and other features and advantages of the present embodiments will be more fully understood from the following detailed description of illustrative embodiments taken in conjunction with the accompanying drawings in which:

FIG. 1C discloses SEQ ID NOS 2 and 3, respectively, in order of appearance.

FIG. 5A discloses SEQ ID NO: 4. FIG. 5B discloses SEQ ID NO: 5.

FIG. 9D discloses SEQ ID NOS 6-9, respectively, in order of appearance.

FIG. 12A: Repeat sequences of SP (SEQ ID NO: 31), ST1 (SEQ ID NO: 32), NM (SEQ ID NO: 33), and TD (SEQ ID NO: 34). Bases are colored to indicate the degree of conservation. FIG. 12B: Plasmids used for characterization of Cas9 proteins in E. coli. FIG. 12C: Functional PAMs are depleted from the library when spacer and protospacer match due to Cas9 cutting. FIG. 12D: Cas9 does not cut when the targeting plasmid spacer and the library protospacer do not match. FIG. 12D: Nonfunctional PAMs are never cut or depleted. FIG. 12F: Selection scheme to identify PAMs. Cells expressing a Cas9 protein and one of two spacer-containing targeting plasmids were transformed with one of two libraries with corresponding protospacers and subjected to antibiotic selection. Surviving uncleaved plasmids were subjected to deep sequencing. Cas9-mediated PAM depletion was quantified by comparing the relative abundance of each sequence within the matched versus the mismatched protospacer libraries.

FIG. 14A: Reporter plasmid used to quantify repression. FIG. 14B: Normalized cellular fluorescence for matched and mismatched spacer-protospacer pairs. Error bars represent the standard deviation across five replicates.

FIG. 16A: A homologous recombination assay was used to quantify gene editing efficiency. Cas9-mediated double-strand breaks within the protospacer stimulated repair of the interrupted GFP cassette using the donor template, yielding cells with intact GFP. Three different templates were used in order to provide the correct PAM for each Cas9. Fluorescent cells were quantified by flow cytometry. FIG. 16A discloses SEQ ID NOS 37-39, respectively, in order of appearance. FIG. 16B: Cell sorting results for NM, ST1, and TD in combination with each of their respective sgRNAs. The protospacer and PAM sequence (SEQ ID NOS 37-39, respectively, in order of appearance) for each Cas9 are displayed above each set. Repair efficiencies are indicated in the upper-right corner of each plot.

FIG. 17A: Reporter constructs for transcriptional activation featured a minimal promoter driving tdTomato. Protospacer and PAM sequences (SEQ ID NOS 37-39, respectively, in order of appearance) were placed upstream of the minimal promoter. Nuclease-null Cas9-VP64 fusion proteins binding to the protospacers resulted in transcriptional activation and enhanced fluorescence. FIG. 17B: Cells transfected with all combinations of Cas9 activator and sgRNA and tdTomato fluorescence visualized. Transcriptional activation occurred only when each Cas9 was paired with its own sgRNA.

DETAILED DESCRIPTION

Figure 1:
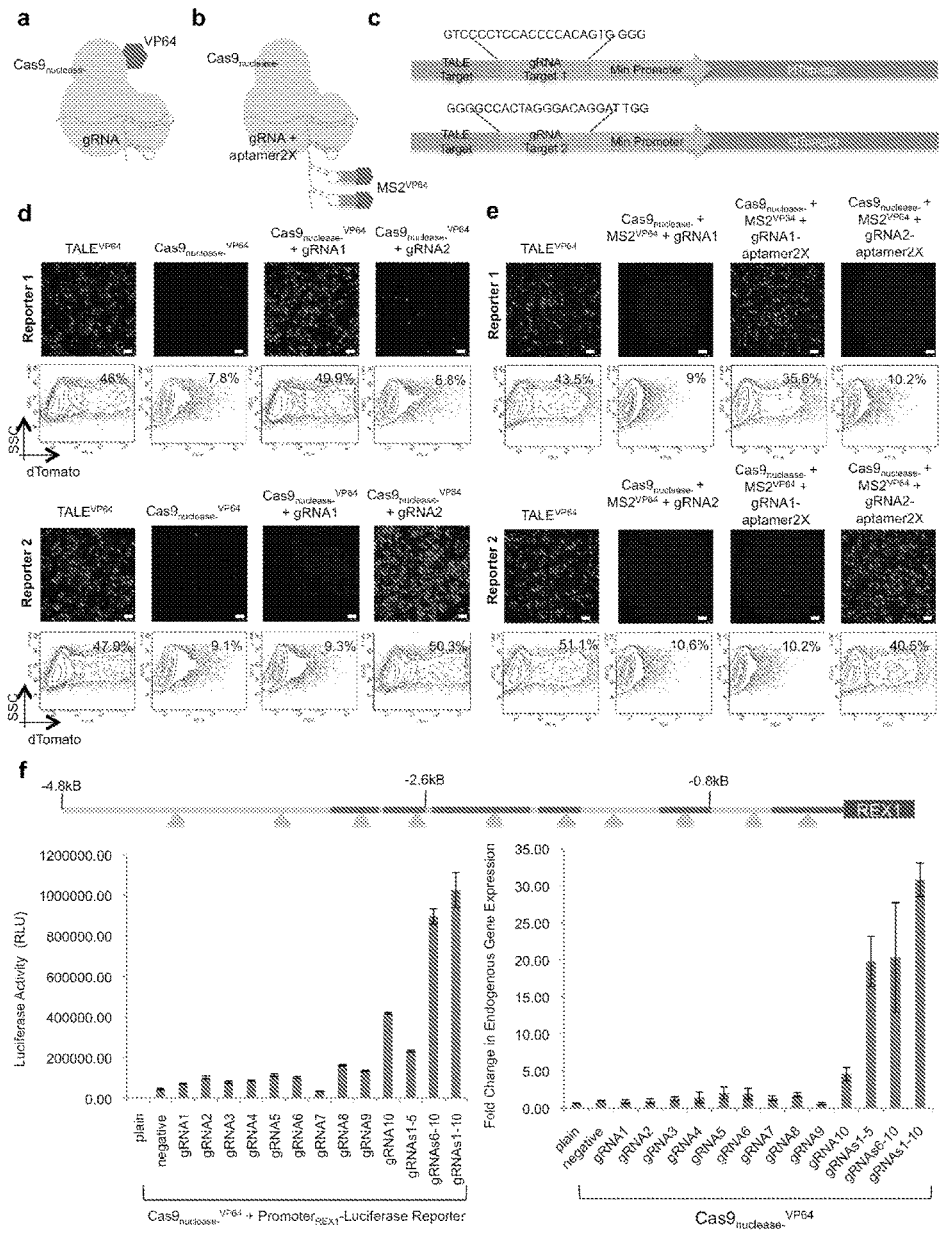
FIG. 1A and FIG. 1B are schematics of RNA-guided transcriptional activation.
FIG. 1C is a design of a reporter construct.
FIG. 1D shows data demonstrating that Cas9N-VP64 fusions display RNA-guided transcriptional activation as assayed by both fluorescence-activated cell sorting (FACS) and immunofluorescence assays (IF).
FIG. 1E shows assay data by FACS and IF demonstrating gRNA sequence-specific transcriptional activation from reporter constructs in the presence of Cas9N, MS2-VP64 and gRNA bearing the appropriate MS2 aptamer binding sites.
FIG. 1F depicts data demonstrating transcriptional induction by individual gRNAs and multiple gRNAs.

Supporting references listed herein may be referred to by superscript. It is to be understood that the superscript refers to the reference as if fully set forth to support a particular statement.

The CRISPR-Cas systems of bacteria and archaea confer acquired immunity by incorporating fragments of viral or plasmid DNA into CRISPR loci and utilizing the transcribed crRNAs to guide nucleases to degrade homologous sequences[1, 2]. In Type II CRISPR systems, a ternary complex of Cas9 nuclease with crRNA and tracrRNA (transactivating crRNA) binds to and cleaves dsDNA protospacer sequences that match the crRNA spacer and also contain a short protospacer-adjacent motif (PAM)[3, 4]. Fusing the crRNA and tracrRNA produces a single guide RNA (sgRNA) that is sufficient to target Cas9[4].

As an RNA-guided nuclease and nickase, Cas9 has been adapted for targeted gene editing[5-9] and selection[10] in a variety of organisms. While these successes are arguably transformative, nuclease-null Cas9 variants are useful for regulatory purposes, as the ability to localize proteins and RNA to nearly any set of dsDNA sequences affords tremendous versatility for controlling biological systems[11-17]. Beginning with targeted gene repression through promoter and 5'-UTR obstruction in bacteria[18], Cas9-mediated regulation is extended to transcriptional activation by means of VP64[19] recruitment in human cells. According to certain aspects the DNA binding proteins described herein, including the orthogonal RNA guided DNA binding proteins such as orthogonal Cas9 proteins, may be used with transcriptional activators, repressors, fluorescent protein labels, chromosome tethers, and numerous other tools known to those of skill in the art. According to this aspect, use of orthogonal Cas9 allows genetic modification using any and all of transcriptional activators, repressors, fluorescent protein labels, chromosome tethers, and numerous other tools known to those of skill in the art. Accordingly, aspect of the present disclosure are directed to the use of orthogonal Cas9 proteins for multiplexed RNA-guided transcriptional activation, repression, and gene editing.

Embodiments of the present disclosure are directed to characterizing and demonstrating orthogonality between multiple Cas9 proteins in bacteria and human cells. Such orthogonal RNA guided DNA binding proteins may be used in a plurality or set to simultaneously and independently regulate transcription, label or edit a plurality of genes in DNA of individual cells.

According to one aspect, a plurality of orthogonal Cas9 proteins are identified from within a single family of CRISPR systems. Though clearly related, exemplary Cas9 proteins from *S. pyogenes, N. meningitidis, S. thermophilus*, and *T. denticola* range from 3.25 to 4.6 kb in length and recognize completely different PAM sequences.

Embodiments of the present disclosure are based on the use of DNA binding proteins to co-localize transcriptional regulator proteins or domains to DNA in a manner to regulate a target nucleic acid. Such DNA binding proteins are readily known to those of skill in the art to bind to DNA for various purposes. Such DNA binding proteins may be naturally occurring. DNA binding proteins included within the scope of the present disclosure include those which may be guided by RNA, referred to herein as guide RNA. According to this aspect, the guide RNA and the RNA guided DNA binding protein form a co-localization complex at the DNA. According to certain aspects, the DNA binding protein may be a nuclease-null DNA binding protein. According to this aspect, the nuclease-null DNA binding protein may result from the alteration or modification of a DNA binding protein having nuclease activity. Such DNA binding proteins having nuclease activity are known to those of skill in the art, and include naturally occurring DNA binding proteins having nuclease activity, such as Cas9 proteins present, for example, in Type II CRISPR systems. Such Cas9 proteins and Type II CRISPR systems are well documented in the art. See Makarova et al., *Nature Reviews, Microbiology*, Vol. 9, June 2011, pp. 467-477 including all supplementary information hereby incorporated by reference in its entirety.

According to a certain aspect, methods are provided to identify two or more or a plurality or a set of orthogonal DNA binding proteins, such as orthogonal RNA guided DNA binding proteins, such as orthogonal RNA guided DNA binding proteins of a Type II CRISPR system, such as orthogonal cas9 proteins, each of which may be nuclease active or nuclease null. According to certain aspects, two or more or a plurality or a set of orthogonal DNA binding proteins may be used with corresponding guide RNAs to simultaneously and independently regulate genes or edit nucleic acids within a cell. According to certain aspects, nucleic acids may be introduced into the cell which encode for the two or more or a plurality or a set of orthogonal DNA binding proteins, the corresponding guide RNAs and two or more or a plurality or a set of corresponding transcriptional regulators or domains. In this manner, many genes may be target in parallel within the same cell for regulation or editing. Methods of editing genomic DNA are well known to those of skill in the art.

Exemplary DNA binding proteins having nuclease activity function to nick or cut double stranded DNA. Such nuclease activity may result from the DNA binding protein having one or more polypeptide sequences exhibiting nuclease activity. Such exemplary DNA binding proteins may have two separate nuclease domains with each domain responsible for cutting or nicking a particular strand of the double stranded DNA. Exemplary polypeptide sequences having nuclease activity known to those of skill in the art include the McrA-HNH nuclease related domain and the RuvC-like nuclease domain. Accordingly, exemplary DNA binding proteins are those that in nature contain one or more of the McrA-HNH nuclease related domain and the RuvC-like nuclease domain According to certain aspects, the DNA binding protein is altered or otherwise modified to inactivate the nuclease activity. Such alteration or modification includes altering one or more amino acids to inactivate the nuclease activity or the nuclease domain. Such modification includes removing the polypeptide sequence or polypeptide sequences exhibiting nuclease activity, i.e. the nuclease domain, such that the polypeptide sequence or polypeptide sequences exhibiting nuclease activity, i.e. nuclease domain, are absent from the DNA binding protein. Other modifications to inactivate nuclease activity will be readily apparent to one of skill in the art based on the present disclosure. Accordingly, a nuclease-null DNA binding protein includes polypeptide sequences modified to inactivate nuclease activity or removal of a polypeptide sequence or sequences to inactivate nuclease activity. The nuclease-null DNA binding protein retains the ability to bind to DNA even though the nuclease activity has been inactivated. Accordingly, the DNA binding protein includes the polypeptide sequence or sequences required for DNA binding but may lack the one or more or all of the nuclease sequences exhibiting nuclease activity. Accordingly, the DNA binding protein includes the polypeptide sequence or sequences required for DNA binding but may have one or more or all of the nuclease sequences exhibiting nuclease activity inactivated.

According to one aspect, a DNA binding protein having two or more nuclease domains may be modified or altered to inactivate all but one of the nuclease domains. Such a modified or altered DNA binding protein is referred to as a DNA binding protein nickase, to the extent that the DNA binding protein cuts or nicks only one strand of double stranded DNA. When guided by RNA to DNA, the DNA binding protein nickase is referred to as an RNA guided DNA binding protein nickase.

An exemplary DNA binding protein is an RNA guided DNA binding protein of a Type II CRISPR System which lacks nuclease activity. An exemplary DNA binding protein is a nuclease-null Cas9 protein. An exemplary DNA binding protein is a Cas9 protein nickase.

In *S. pyogenes*, Cas9 generates a blunt-ended double-stranded break 3 bp upstream of the protospacer-adjacent motif (PAM) via a process mediated by two catalytic domains in the protein: an HNH domain that cleaves the complementary strand of the DNA and a RuvC-like domain that cleaves the non-complementary strand. See Jinke et al., Science 337, 816-821 (2012) hereby incorporated by reference in its entirety. Cas9 proteins are known to exist in many Type II CRISPR systems including the following as identified in the supplementary information to Makarova et al., Nature Reviews, Microbiology, Vol. 9, June 2011, pp. 467-477: *Methanococcus maripaludis* C7; *Corynebacterium diphtheriae*; *Corynebacterium efficiens* YS-314; *Corynebacterium glutamicum* ATCC 13032 Kitasato; *Corynebacterium glutamicum* ATCC 13032 Bielefeld; *Corynebacterium glutamicum* R; *Corynebacterium kroppenstedtii* DSM 44385; *Mycobacterium abscessus* ATCC 19977; *Nocardia farcinica* IFM10152; *Rhodococcus erythropolis* PR4; *Rhodococcus jostii* RHA1; *Rhodococcus opacus* B4 uid36573; *Acidothermus cellulolyticus* 11B; *Arthrobacter chlorophenolicus* A6; *Kribbella flavida* DSM 17836 uid43465; *Thermomonospora curvata* DSM 43183; *Bifidobacterium dentium* Bd1; *Bifidobacterium longum* DJO10A; *Slackia heliotrinireducens* DSM 20476; *Persephonella marina* EX H1; *Bacteroides fragilis* NCTC 9434; *Capnocytophaga ochracea* DSM 7271; *Flavobacterium psychrophilum* JIP02 86; *Akkermansia muciniphila* ATCC BAA 835; *Roseiflexus castenholzii* DSM 13941; *Roseiflexus* RS1; *Synechocystis* PCC6803; *Elusimicrobium minutum* Pei191; uncultured Termite group 1 bacterium phylotype Rs D17; *Fibrobacter succinogenes* S85; *Bacillus cereus* ATCC 10987; *Listeria innocua*; *Lactobacillus casei*; *Lactobacillus rhamnosus* GG; *Lactobacillus salivarius* UCC118; *Streptococcus agalactiae* A909; *Streptococcus agalactiae* NEM316; *Streptococcus agalactiae* 2603; *Streptococcus dysgalactiae equisimilis* GGS 124; *Streptococcus equi zooepidemicus* MGCS10565; *Streptococcus gallolyticus* UCN34 uid46061; *Streptococcus gordonii* Challis subst CH1; *Streptococcus mutans* NN2025 uid46353; *Streptococcus mutans*; *Streptococcus pyogenes* M1 GAS; *Streptococcus pyogenes* MGAS5005; *Streptococcus pyogenes* MGAS2096; *Streptococcus pyogenes* MGAS9429; *Streptococcus pyogenes* MGAS10270; *Streptococcus pyogenes* MGAS6180; *Streptococcus pyogenes* MGAS315; *Streptococcus pyogenes* SSI-1; *Streptococcus pyogenes* MGAS10750; *Streptococcus pyogenes* NZ131; *Streptococcus thermophiles* CNRZ1066; *Streptococcus thermophiles* LMD-9; *Streptococcus thermophiles* LMG 18311; *Clostridium botulinum* A3 Loch Maree; *Clostridium botulinum* B Eklund 17B; *Clostridium botulinum* Ba4 657; *Clostridium botulinum* F Langeland; *Clostridium cellulolyticum* H10; *Finegoldia magna* ATCC 29328; *Eubacterium rectale* ATCC 33656; *Mycoplasma gallisepticum*; *Mycoplasma* mobile 163K; *Mycoplasma penetrans*; *Mycoplasma synoviae* 53; *Streptobacillus moniliformis* DSM 12112; *Bradyrhizobium* BTAi1; *Nitrobacter hamburgensis* X14; *Rhodopseudomonas palustris* BisB18; *Rhodopseudomonas palustris* BisB5; *Parvibaculum lavamentivorans* DS-1; *Dinoroseobacter shibae* DFL 12; *Gluconacetobacter diazotrophicus* Pal 5 FAPERJ; *Gluconacetobacter diazotrophicus* Pal 5 JGI; *Azospirillum* B510 uid46085; *Rhodospirillum rubrum* ATCC 11170; *Diaphorobacter* TPSY uid29975; *Verminephrobacter eiseniae* EF01-2; *Neisseria meningitides* 053442; *Neisseria meningitides* alpha14; *Neisseria meningitides* Z2491; *Desulfovibrio salexigens* DSM 2638; *Campylobacter jejuni doylei* 269 97; *Campylobacter jejuni* 81116; *Campylobacter jejuni*; *Campylobacter lari* RM2100; *Helicobacter hepaticus*; *Wolinella succinogenes*; *Tolumonas auensis* DSM 9187; *Pseudoalteromonas atlantica* T6c; *Shewanella pealeana* ATCC 700345; *Legionella pneumophila* Paris; *Actinobacillus succinogenes* 130Z; *Pasteurella multocida*; *Francisella tularensis novicida* U112; *Francisella tularensis holarctica*; *Francisella tularensis* FSC 198; *Francisella tularensis tularensis*; *Francisella tularensis* WY96-3418; and *Treponema denticola* ATCC 35405. Accordingly, aspects of the present disclosure are directed to a Cas9 protein present in a Type II CRISPR system, which has been rendered nuclease null or which has been rendered a nickase as described herein.

The Cas9 protein may be referred by one of skill in the art in the literature as Csn1. The *S. pyogenes* Cas9 protein sequence that is the subject of experiments described herein is shown below. See Deltcheva et al., Nature 471, 602-607 (2011) hereby incorporated by reference in its entirety.
MDKKYSIGLDIGTNSVGWAVITDEYKVPSKKFKVL-GNTDRHSIKKNLIGALLFDSGETAE ATRLKRTAR-RRYTRRKNRICYLQEIFSNEMAKVDDSFFHRLEES-FLVEEDKKHERHPIFG
NIVDEVAYHEKYPTIYHLRKKLVDSTDKADLRLIYL-ALAHMIKFRGHFLIEGDLNPDNSD VDKLFIQLVQ-TYNQLFEENPINASGVDAKAILSARLSKSRRLENLIA-QLPGEKKNGLFGN
LIALSLGLTPNFKSNFDLAEDAKLQLSKDTYDD-DLDNLLAQIGDQYADLFLAAKNLSDAI LLSDIL-RVNTEITKAPLSASMIKRYDEHHQDLTLLKA-LVRQQLPEKYKEIFFDQSKNGYA
GYIDGGASQEEFYKFIKPILEKMDGTEELLVKL-NREDLLRKQRTFDNGSIPHQIHLGELH AILRRQED-FYPFLKDNREKIEKILTFRIPYYVGPLARGNSRFAW-MTRKSEETITPWNFEE
VVDKGASAQSFIERMTNFDKNLPNEKVLPKHSLLY-EYFTVYNELTKVKYVTEGMRKPAFL SGEQK-KAIVDLLFKTNRKVTVKQLKEDYFKKIECFDSVEIS-GVEDRFNASLGTYHDLLKI
IKDKDFLDNEENEDILEDIVLTLTLFEDREMIEERLK-TYAHLFDDKVMKQLKRRRYTGWG RLSRKLINGIRD-KQSGKTILDFLKSDGFANRNFMQLIHDDSLT-FKEDIQKAQVSGQGDSL
HEHIANLAGSPAIKKGILQTVKVVDELVKVMGRHK-PENIVIEMARENQTTQKGQKNSRER MKRIEEGIKEL-GSQILKEHPVENTQLQNEKLYLYYLQNGRD-MYVDQELDINRLSDYDVDH
IVPQSFLKDDSIDNKVLTRSDKNRGKSDNVP-SEEVVKKMKNYWRQLLNAKLITQRKFDNL TKAERGGLSELDKAGFIKRQLVETRQITKHVAQILD-SRMNTKYDENDKLIREVKVITLKS KLVSDFRKDFQ-FYKVREINNYHHAHDAYLNAVVGTALIKKYP-KLESEFVYGDYKVYDVRK
MIAKSEQEIGKATAKYFFYSNIMNFFKTEIT-LANGEIRKRPLIETNGETGEIVWDKGRDF ATVRKV-LSMPQVNIVKKTEVQTGGFSKESILPKRNSDKLIARK-KDWDPKKYGGFDSPTVA
YSVLVVAKVEKGKSKKLKSVKELLGITIMERSS-FEKNPIDFLEAKGYKEVKKDLIIKLPK YSLFE-LENGRKRMLASAGELQKGNELALPSKYVNFLY-LASHYEKLKGSPEDNEQKQLFVE QHKHYLDEIIEQISEFSKRVILADANLDKVL-SAYNKHRDKPIREQAENIIHLFTLTNLGA PAAF-KYFDTTIDRKRYTSTKEVLDATLIHQSITGLY-ETRIDLSQLGGD- (SEQ ID NO: 1)

According to certain aspects of methods of RNA-guided genome regulation described herein, Cas9 is altered to reduce, substantially reduce or eliminate nuclease activity. Such a Cas9 may be an orthogonal Cas9, such as when more than one Cas9 proteins are envisioned. In this context, two or more or a plurality or set of orthogonal Cas9 proteins may be used in the methods described herein. According to one aspect, Cas9 nuclease activity is reduced, substantially reduced or eliminated by altering the RuvC nuclease domain or the HNH nuclease domain According to one aspect, the RuvC nuclease domain is inactivated. According to one aspect, the HNH nuclease domain is inactivated. According to one aspect, the RuvC nuclease domain and the HNH nuclease domain are inactivated. According to an additional aspect, Cas9 proteins are provided where the RuvC nuclease domain and the HNH nuclease domain are inactivated. According to an additional aspect, nuclease-null Cas9 proteins are provided insofar as the RuvC nuclease domain and the HNH nuclease domain are inactivated. According to an additional aspect, a Cas9 nickase is provided where either the RuvC nuclease domain or the HNH nuclease domain is inactivated, thereby leaving the remaining nuclease domain active for nuclease activity. In this manner, only one strand of the double stranded DNA is cut or nicked.

According to an additional aspect, nuclease-null Cas9 proteins are provided where one or more amino acids in Cas9 are altered or otherwise removed to provide nuclease-null Cas9 proteins. According to one aspect, the amino acids include D10 and H840. See Jinke et al., *Science* 337, 816-821 (2012). According to an additional aspect, the amino acids include D839 and N863. According to one aspect, one or more or all of D10, H840, D839 and H863 are substituted with an amino acid which reduces, substantially eliminates or eliminates nuclease activity. According to one aspect, one or more or all of D10, H840, D839 and H863 are substituted with alanine. According to one aspect, a Cas9 protein having one or more or all of D10, H840, D839 and H863 substituted with an amino acid which reduces, substantially eliminates or eliminates nuclease activity, such as alanine, is referred to as a nuclease-null Cas9 or Cas9N and exhibits reduced or eliminated nuclease activity, or nuclease activity is absent or substantially absent within levels of detection. According to this aspect, nuclease activity for a Cas9N may be undetectable using known assays, i.e. below the level of detection of known assays.

According to one aspect, the nuclease null Cas9 protein includes homologs and orthologs thereof which retain the ability of the protein to bind to the DNA and be guided by the RNA. According to one aspect, the nuclease null Cas9 protein includes the sequence as set forth for naturally occurring Cas9 from *S. pyogenes* and having one or more or all of D10, H840, D839 and H863 substituted with alanine and protein sequences having at least 30%, 40%, 50%, 60%, 70%, 80%, 90%, 95%, 98% or 99% homology thereto and being a DNA binding protein, such as an RNA guided DNA binding protein.

According to one aspect, the nuclease null Cas9 protein includes the sequence as set forth for naturally occurring Cas9 from *S. pyogenes* excepting the protein sequence of the RuvC nuclease domain and the HNH nuclease domain and also protein sequences having at least 30%, 40%, 50%, 60%, 70%, 80%, 90%, 95%, 98% or 99% homology thereto and being a DNA binding protein, such as an RNA guided DNA binding protein. In this manner, aspects of the present disclosure include the protein sequence responsible for DNA binding, for example, for co-localizing with guide RNA and binding to DNA and protein sequences homologous thereto, and need not include the protein sequences for the RuvC nuclease domain and the HNH nuclease domain (to the extent not needed for DNA binding), as these domains may be either inactivated or removed from the protein sequence of the naturally occurring Cas9 protein to produce a nuclease null Cas9 protein.

Figure 4:
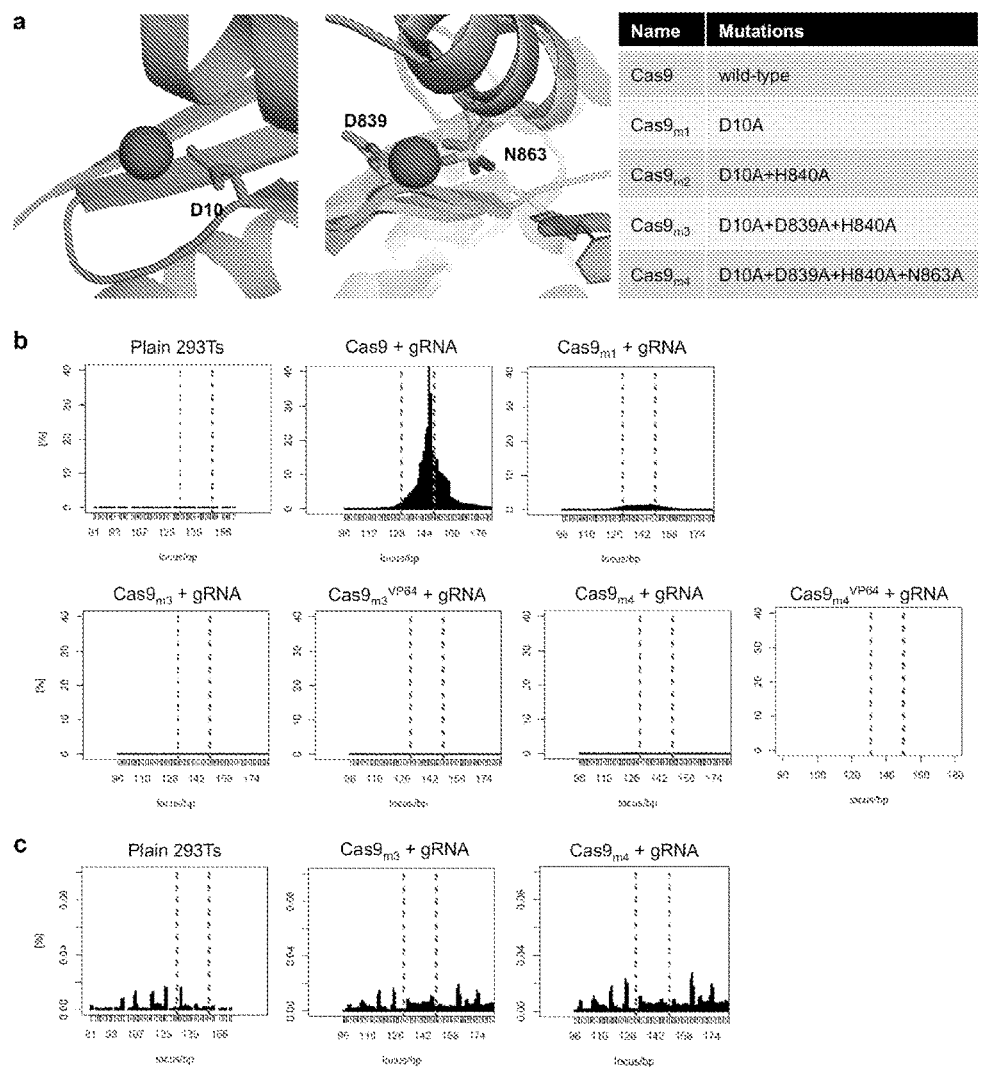
FIG. 4A is a schematic of a metal coordinating residue in RuvC PDB ID: 4EP4 (blue) position D7 (left), a schematic of HNH endonuclease domains from PDB IDs: 3M7K (orange) and 4H9D (cyan) including a coordinated Mg-ion (gray sphere) and DNA from 3M7K (purple) (middle) and a list of mutants analyzed (right).
FIG. 4B depicts data showing undetectable nuclease activity for Cas9 mutants m3 and m4, and also their respective fusions with VP64.
FIG. 4C is a higher-resolution examination of the data in FIG. 4B.

For purposes of the present disclosure, FIG. 4A depicts metal coordinating residues in known protein structures with homology to Cas9. Residues are labeled based on position in Cas9 sequence. Left: RuvC structure, PDB ID: 4EP4 (blue) position D7, which corresponds to D10 in the Cas9 sequence, is highlighted in a Mg-ion coordinating position. Middle: Structures of HNH endonuclease domains from PDB IDs: 3M7K (orange) and 4H9D (cyan) including a coordinated Mg-ion (gray sphere) and DNA from 3M7K (purple). Residues D92 and N113 in 3M7K and 4H9D positions D53 and N77, which have sequence homology to Cas9 amino acids D839 and N863, are shown as sticks. Right: List of mutants made and analyzed for nuclease activity: Cas9 wildtype; $Cas9_{m1}$ which substitutes alanine for D10; $Cas9_{m2}$ which substitutes alanine for D10 and alanine for H840; $Cas9_{m3}$ which substitutes alanine for D10, alanine for H840, and alanine for D839; and $Cas9_{m4}$ which substitutes alanine for D10, alanine for H840, alanine for D839, and alanine for N863.

As shown in FIG. 4B, the Cas9 mutants: m3 and m4, and also their respective fusions with VP64 showed undetectable nuclease activity upon deep sequencing at targeted loci. The plots show the mutation frequency versus genomic position, with the red lines demarcating the gRNA target. FIG. 4C is a higher-resolution examination of the data in FIG. 4B and confirms that the mutation landscape shows comparable profile as unmodified loci.

According to one aspect, an engineered Cas9-gRNA system is provided which enables RNA-guided genome regulation in human cells by tethering transcriptional activation domains to either a nuclease-null Cas9 or to guide RNAs. According to one aspect of the present disclosure, one or more transcriptional regulatory proteins or domains (such terms are used interchangeably) are joined or otherwise connected to a nuclease-deficient Cas9 or one or more guide RNA (gRNA). The transcriptional regulatory domains correspond to targeted loci. Accordingly, aspects of the present disclosure include methods and materials for localizing transcriptional regulatory domains to targeted loci by fusing, connecting or joining such domains to either Cas9N or to the gRNA.

According to one aspect, a Cas9N-fusion protein capable of transcriptional activation is provided. According to one aspect, a VP64 activation domain (see Zhang et al., *Nature Biotechnology* 29, 149-153 (2011) hereby incorporated by reference in its entirety) is joined, fused, connected or otherwise tethered to the C terminus of Cas9N. According to one method, the transcriptional regulatory domain is provided to the site of target genomic DNA by the Cas9N protein. According to one method, a Cas9N fused to a transcriptional regulatory domain is provided within a cell along with one or more guide RNAs. The Cas9N with the transcriptional regulatory domain fused thereto bind at or near target genomic DNA. The one or more guide RNAs bind at or near target genomic DNA. The transcriptional regulatory domain regulates expression of the target gene. According to a specific aspect, a Cas9N-VP64 fusion activated transcription of reporter constructs when combined with gRNAs targeting sequences near the promoter, thereby displaying RNA-guided transcriptional activation.

According to one aspect, a gRNA-fusion protein capable of transcriptional activation is provided. According to one aspect, a VP64 activation domain is joined, fused, connected or otherwise tethered to the gRNA. According to one method, the transcriptional regulatory domain is provided to the site of target genomic DNA by the gRNA. According to one method, a gRNA fused to a transcriptional regulatory domain is provided within a cell along with a Cas9N protein. The Cas9N binds at or near target genomic DNA. The one or more guide RNAs with the transcriptional regulatory protein or domain fused thereto bind at or near target genomic DNA. The transcriptional regulatory domain regulates expression of the target gene. According to a specific aspect, a Cas9N protein and a gRNA fused with a transcriptional regulatory domain activated transcription of reporter constructs, thereby displaying RNA-guided transcriptional activation.

Figure 5:
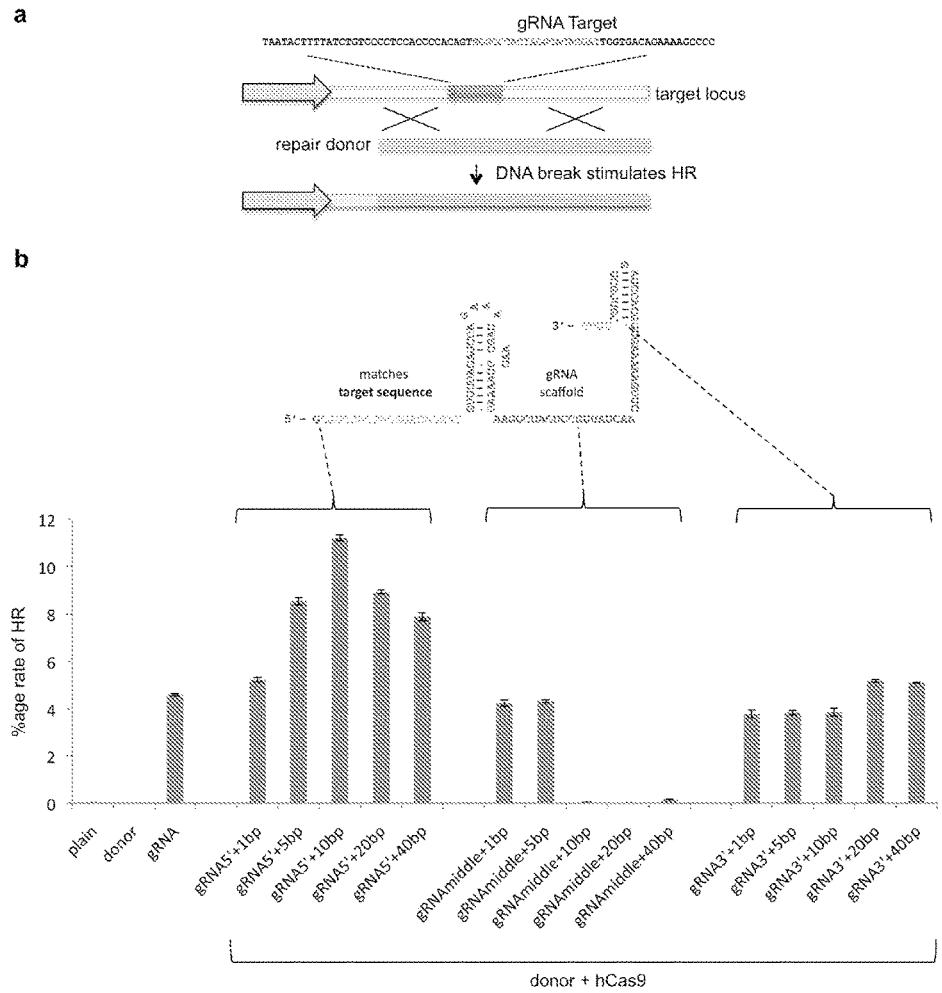
FIG. 5A is a schematic of a homologous recombination assay to determine Cas9-gRNA activity.
FIG. 5B depicts guide RNAs with random sequence insertions and percentage rate of homologous recombination.

The gRNA tethers capable of transcriptional regulation were constructed by identifying which regions of the gRNA will tolerate modifications by inserting random sequences into the gRNA and assaying for Cas9 function. gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. See FIG. 5A-5B summarizing gRNA flexibility to random base insertions. FIG. 5A is a schematic of a homologous recombination (HR) assay to determine Cas9-gRNA activity. As shown in FIG. 5B, gRNAs bearing random sequence insertions at either the 5' end of the crRNA portion or the 3' end of the tracrRNA portion of a chimeric gRNA retain functionality, while insertions into the tracrRNA scaffold portion of the chimeric gRNA result in loss of function. The points of insertion in the gRNA sequence are indicated by red nucleotides. Without wishing to be bound by scientific theory, the increased activity upon random base insertions at the 5' end may be due to increased half-life of the longer gRNA.

To attach VP64 to the gRNA, two copies of the MS2 bacteriophage coat-protein binding RNA stem-loop were appended to the 3' end of the gRNA. See Fusco et al., *Current Biology*: CB13, 161-167 (2003) hereby incorporated by reference in its entirety. These chimeric gRNAs were expressed together with Cas9N and MS2-VP64 fusion protein. Sequence-specific transcriptional activation from reporter constructs was observed in the presence of all 3 components.

FIG. 1A is a schematic of RNA-guided transcriptional activation. As shown in FIG. 1A, to generate a Cas9N-fusion protein capable of transcriptional activation, the VP64 activation domain was directly tethered to the C terminus of Cas9N. As shown in FIG. 1B, to generate gRNA tethers capable of transcriptional activation, two copies of the MS2 bacteriophage coat-protein binding RNA stem-loop were appended to the 3' end of the gRNA. These chimeric gRNAs were expressed together with Cas9N and MS2-VP64 fusion protein. FIG. 1C shows design of reporter constructs used to assay transcriptional activation. The two reporters bear distinct gRNA target sites, and share a control TALE-TF target site. As shown in FIG. 1D, Cas9N-VP64 fusions display RNA-guided transcriptional activation as assayed by both fluorescence-activated cell sorting (FACS) and immunofluorescence assays (IF). Specifically, while the control TALE-TF activated both reporters, the Cas9N-VP64 fusion activates reporters in a gRNA sequence specific manner. As shown in FIG. 1E, gRNA sequence-specific transcriptional activation from reporter constructs only in the presence of all 3 components: Cas9N, MS2-VP64 and gRNA bearing the appropriate MS2 aptamer binding sites was observed by both FACS and IF.

Figure 10:
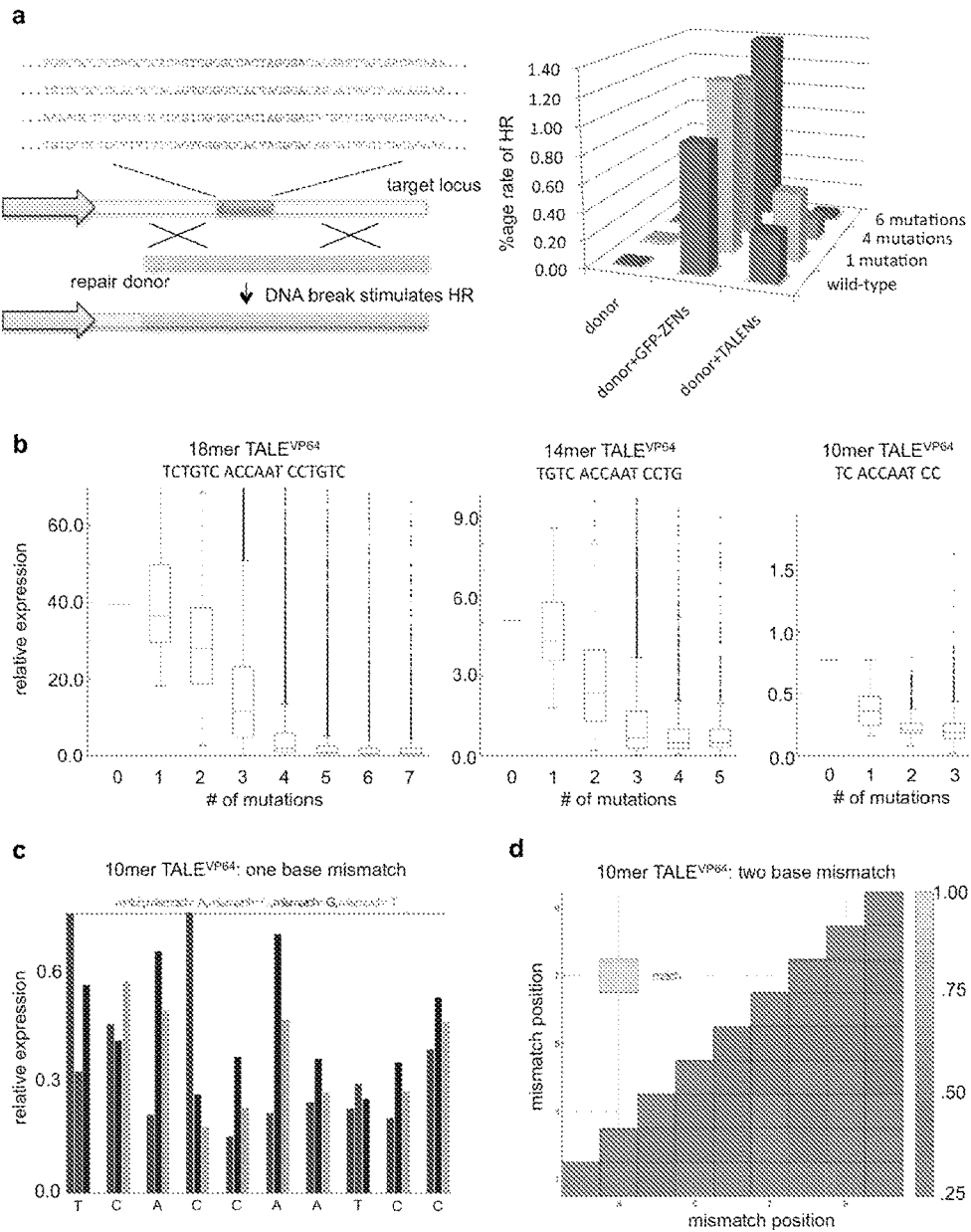
FIG. 10A depicts data from a nuclease mediated HR assay confirming that 18-mer TALEs tolerate multiple mutations in their target sequences (SEQ ID NOS 10-13, respectively, in order of appearance).
FIG. 10B depicts data from analysis of the targeting landscape of TALEs of 3 different sizes (18-mer, 14-mer and 10-mer) (SEQ ID NOS 14-16, respectively).
FIG. 10C depicts data for 10-mer TALEs (SEQ ID NO: 16) show near single-base mismatch resolution.
FIG. 10D depicts heat plot data for 10-mer TALEs show near single-base mismatch resolution.

According to certain aspects, methods are provided for regulating endogenous genes using Cas9N, one or more gRNAs and a transcriptional regulatory protein or domain According to one aspect, an endogenous gene can be any desired gene, referred to herein as a target gene. According to one exemplary aspect, genes target for regulation included ZFP42 (REX1) and POU5F1 (OCT4), which are both tightly regulated genes involved in maintenance of pluripotency. As shown in FIG. 1F, 10 gRNAs targeting a ~5 kb stretch of DNA upstream of the transcription start site (DNase hypersensitive sites are highlighted in green) were designed for the REX1 gene. Transcriptional activation was assayed using either a promoter-luciferase reporter construct (see Takahashi et al., Cell 131 861-872 (2007) hereby incorporated by reference in its entirety) or directly via qPCR of the endogenous genes.

Figure 6:
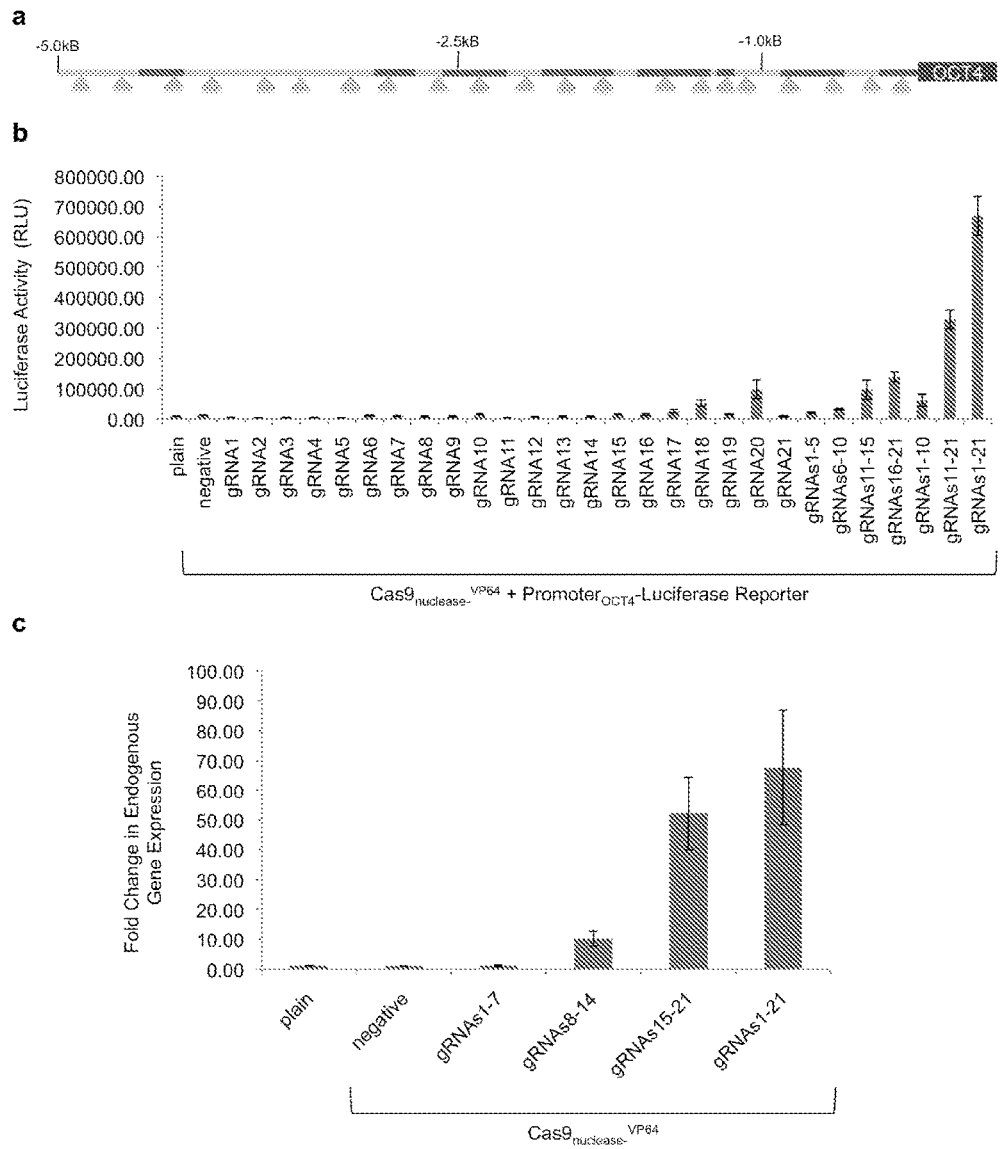
FIG. 6A is a schematic of guide RNAs for the OCT4 gene.
FIG. 6B depicts transcriptional activation for a promoter-luciferase reporter construct.
FIG. 6C depicts transcriptional activation via qPCR of endogenous genes.

FIGS. 6A-6D are directed to RNA-guided OCT4 regulation using Cas9N-VP64. As shown in FIG. 6A, 21 gRNAs targeting a ~5 kb stretch of DNA upstream of the transcription start site were designed for the OCT4 gene. The DNase hypersensitive sites are highlighted in green. FIG. 6B shows transcriptional activation using a promoter-luciferase reporter construct. FIG. 6C shows transcriptional activation directly via qPCR of the endogenous genes. While introduction of individual gRNAs modestly stimulated transcription, multiple gRNAs acted synergistically to stimulate robust multi-fold transcriptional activation.

Figure 7:
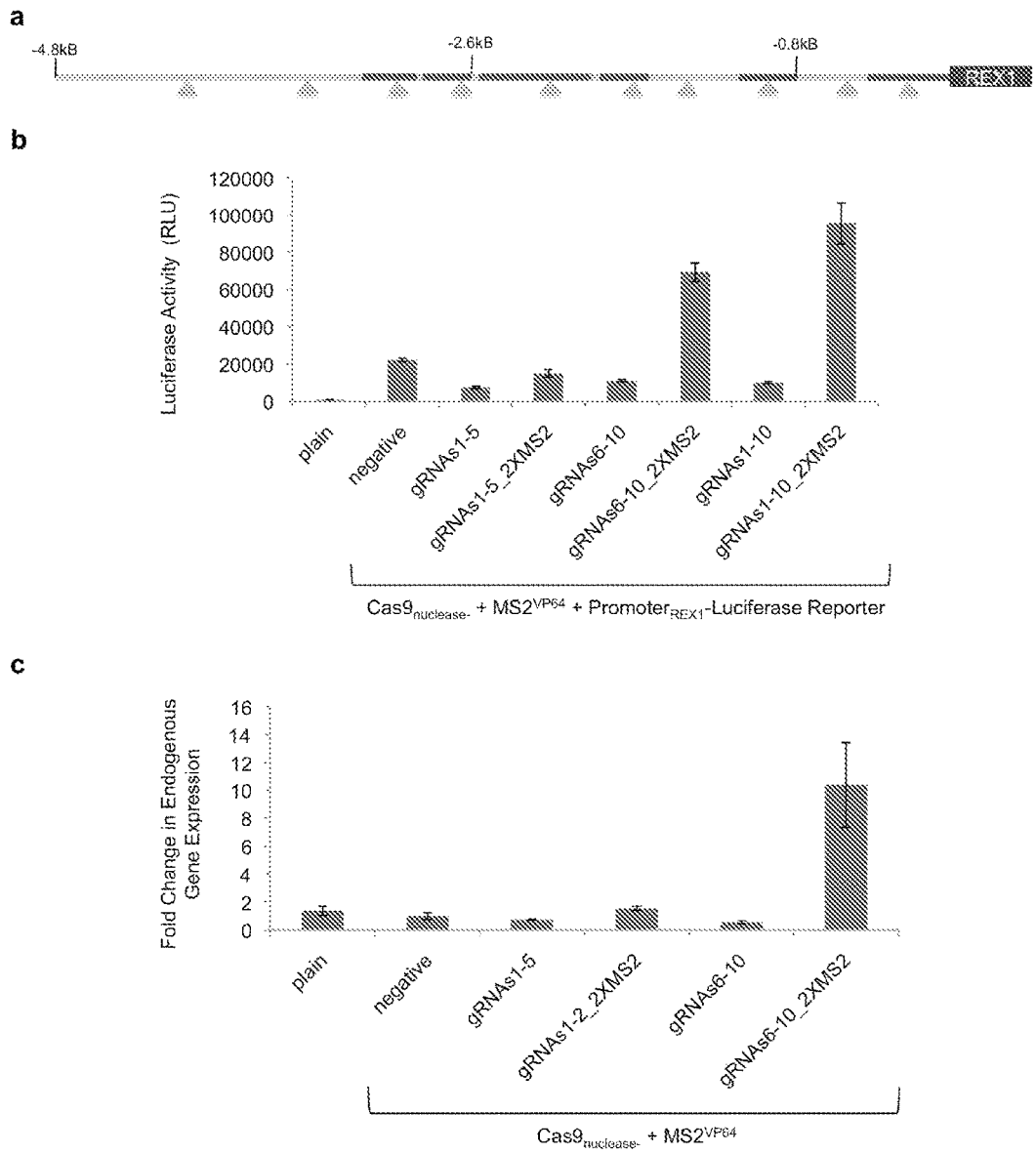
FIG. 7A is a schematic of guide RNAs for the REX1 gene.
FIG. 7B depicts transcriptional activation for a promoter-luciferase reporter construct.
FIG. 7C depicts transcriptional activation via qPCR of endogenous genes.

FIGS. 7A-7C are directed to RNA-guided REX1 regulation using Cas9N, MS2-VP64 and gRNA+2X-MS2 aptamers. As shown in FIG. 7A, 10 gRNAs targeting a ~5 kb stretch of DNA upstream of the transcription start site were designed for the REX1 gene. The DNase hypersensitive sites are highlighted in green. FIG. 7B shows transcriptional activation using a promoter-luciferase reporter construct. FIG. 7C shows transcriptional activation directly via qPCR of the endogenous genes. While introduction of individual gRNAs modestly stimulated transcription, multiple gRNAs acted synergistically to stimulate robust multi-fold transcriptional activation. In one aspect, the absence of the 2X-MS2 aptamers on the gRNA does not result in transcriptional activation. See Maeder et al., *Nature Methods* 10, 243-245 (2013) and Perez-Pinera et al., *Nature Methods* 10, 239-242 (2013) each of which are hereby incorporated by reference in its entirety.

Accordingly, methods are directed to the use of multiple guide RNAs with a Cas9N protein and a transcriptional regulatory protein or domain to regulate expression of a target gene.

Both the Cas9 and gRNA tethering approaches were effective, with the former displaying ~1.5-2 fold higher potency. This difference is likely due to the requirement for 2-component as opposed to 3-component complex assembly. However, the gRNA tethering approach in principle enables different effector domains to be recruited by distinct gRNAs so long as each gRNA uses a different RNA-protein interaction pair. See Karyer-Bibens et al, *Biology of the Cell/Under the Auspices of the European Cell Biology Organization* 100, 125-138 (2008) hereby incorporated by reference in its entirety. According to one aspect of the present disclosure, different target genes may be regulated, using specific guide RNA and, a generic Cas9N protein, i.e. the same or a similar Cas9N protein for different target genes. According to one aspect, methods of multiplex gene regulation are provided using the same or similar Cas9N.

Methods of the present disclosure are also directed to editing target genes using the Cas9N proteins and guide RNAs described herein to provide multiplex genetic and epigenetic engineering of human cells. With Cas9-gRNA targeting being an issue (see Jiang et al., *Nature Biotechnology* 31, 233-239 (2013) hereby incorporated by reference in its entirety), methods are provided for in-depth interrogation of Cas9 affinity for a very large space of target sequence variations. Accordingly, aspects of the present disclosure provide direct high-throughput readout of Cas9 targeting in human cells, while avoiding complications introduced by dsDNA cut toxicity and mutagenic repair incurred by specificity testing with native nuclease-active Cas9.

Further aspects of the present disclosure are directed to the use of DNA binding proteins or systems in general for the transcriptional regulation of a target gene. One of skill in the art will readily identify exemplary DNA binding systems based on the present disclosure. Such DNA binding systems need not have any nuclease activity, as with the naturally occurring Cas9 protein. Accordingly, such DNA binding systems need not have nuclease activity inactivated. One exemplary DNA binding system is TALE. According to one aspect, TALE specificity was evaluated using the methodology shown in FIG. 2A. A construct library in which each element of the library comprises a minimal promoter driving a dTomato fluorescent protein is designed. Downstream of the transcription start site m, a 24 bp (A/C/G) random transcript tag is inserted, while two TF binding sites are placed upstream of the promoter: one is a constant DNA sequence shared by all library elements, and the second is a variable feature that bears a 'biased' library of binding sites which are engineered to span a large collection of sequences that present many combinations of mutations away from the target sequence the programmable DNA targeting complex was designed to bind. This is achieved using degenerate oligonucleotides engineered to bear nucleotide frequencies at each position such that the target sequence nucleotide appears at a 79% frequency and each other nucleotide occurs at 7% frequency. See Patwardhan et al., *Nature Biotechnology* 30, 265-270 (2012) hereby incorporated by reference in its entirety. The reporter library is then sequenced to reveal the associations between the 24 bp dTomato transcript tags and their corresponding 'biased' target site in the library element. The large diversity of the transcript tags assures that sharing of tags between different targets will be extremely rare, while the biased construction of the target sequences means that sites with few mutations will be associated with more tags than sites with more mutations. Next, transcription of the dTomato reporter genes is stimulated with either a control-TF engineered to bind the shared DNA site, or the target-TF that was engineered to bind the target site. The abundance of each expressed transcript tag is measured in each sample by conducting RNAseq on the stimulated cells, which is then mapped back to their corresponding binding sites using the association table established earlier. The control-TF is expected to excite all library members equally since its binding site is shared across all library elements, while the target-TF is expected to skew the distribution of the expressed members to those that are preferentially targeted by it. This assumption is used in step 5 to compute a normalized expression level for each binding site by dividing the tag counts obtained for the target-TF by those obtained for the control-TF.

Figure 2:
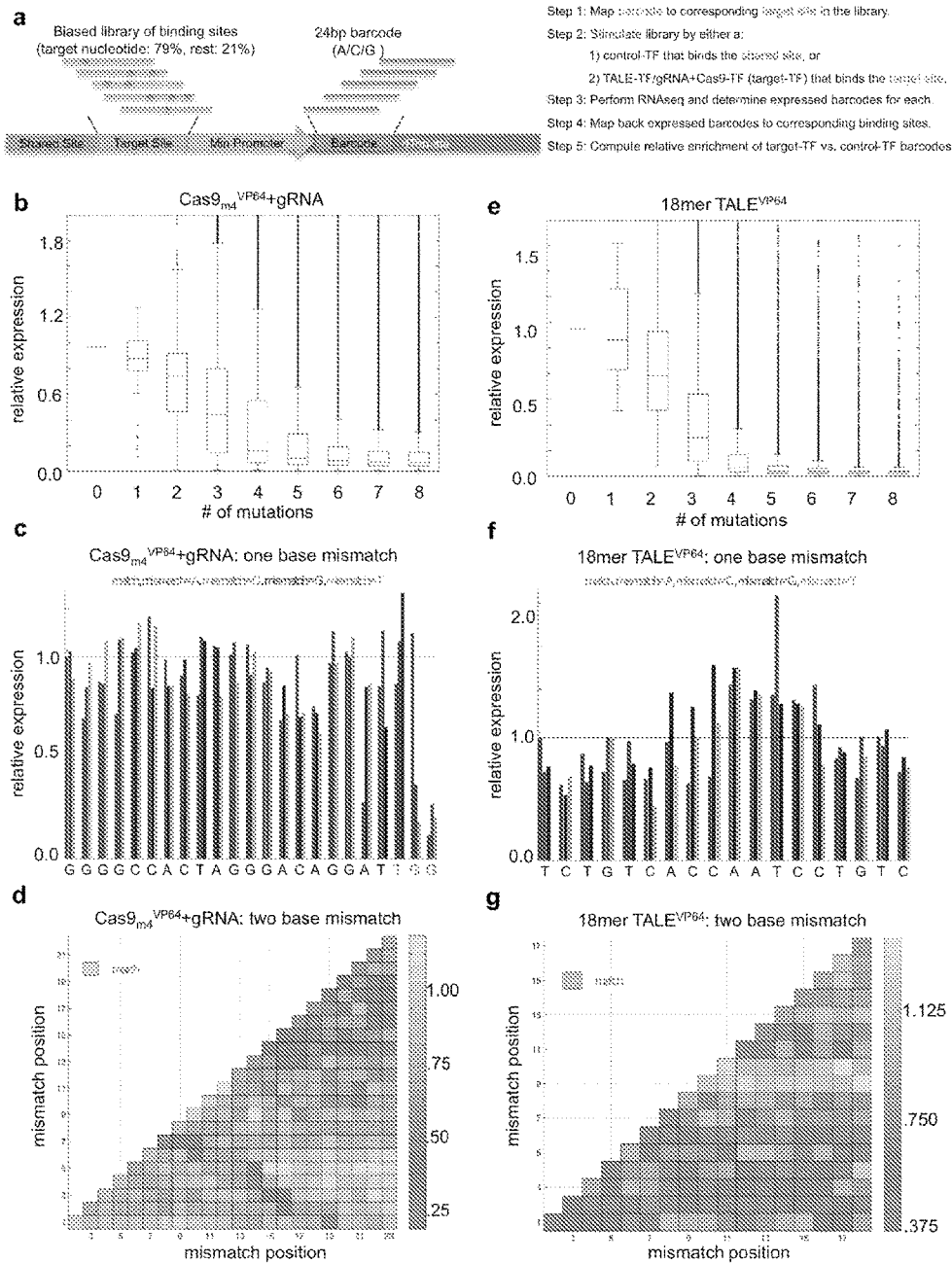
FIG. 2A depicts a methodology for evaluating the landscape of targeting by Cas9-gRNA complexes and TALEs.
FIG. 2B depicts data demonstrating that a Cas9-gRNA complex is on average tolerant to 1-3 mutations in its target sequences.
FIG. 2C depicts data demonstrating that the Cas9-gRNA complex is largely insensitive to point mutations, except those localized to the PAM sequence (SEQ ID NO: 3).
FIG. 2D depicts heat plot data demonstrating that introduction of 2 base mismatches significantly impairs the Cas9-gRNA complex activity.
FIG. 2E depicts data demonstrating that an 18-mer TALE reveals is on average tolerant to 1-2 mutations in its target sequence.
FIG. 2F depicts data demonstrating the 18-mer TALE (SEQ ID NO: 14) is, similar to the Cas9-gRNA complexes, largely insensitive to single base mismatched in its target.
FIG. 2G depicts heat plot data demonstrating that introduction of 2 base mismatches significantly impairs the 18-mer TALE activity.

As shown in FIG. 2B, the targeting landscape of a Cas9-gRNA complex reveals that it is on average tolerant to 1-3 mutations in its target sequences. As shown in FIG. 2C, the Cas9-gRNA complex is also largely insensitive to point mutations, except those localized to the PAM sequence. Notably this data reveals that the predicted PAM for the *S. pyogenes* Cas9 is not just NGG but also NAG. As shown in FIG. 2D, introduction of 2 base mismatches significantly impairs the Cas9-gRNA complex activity, however only when these are localized to the 8-10 bases nearer the 3' end of the gRNA target sequence (in the heat plot the target sequence positions are labeled from 1-23 starting from the 5' end).

The mutational tolerance of another widely used genome editing tool, TALE domains, was determined using the transcriptional specificity assay described herein. As shown in FIG. 2E, the TALE off-targeting data for an 18-mer TALE reveals that it can tolerate on average 1-2 mutations in its target sequence, and fails to activate a large majority of 3 base mismatch variants in its targets. As shown in FIG. 2F, the 18-mer TALE is, similar to the Cas9-gRNA complexes, largely insensitive to single base mismatched in its target. As shown in FIG. 2G, introduction of 2 base mismatches significantly impairs the 18-mer TALE activity. TALE activity is more sensitive to mismatches nearer the 5' end of its target sequence (in the heat plot the target sequence positions are labeled from 1-18 starting from the 5' end).

Results were confirmed using targeted experiments in a nuclease assay which is the subject of FIGS. 10A-10D directed to evaluating the landscape of targeting by TALEs of different sizes. As shown in FIG. 10A, using a nuclease mediated HR assay, it was confirmed that 18-mer TALEs tolerate multiple mutations in their target sequences. As shown in FIG. 10B, using the approach described in FIG. 2A, the targeting landscape of TALEs of 3 different sizes (18-mer, 14-mer and 10-mer) was analyzed. Shorter TALEs (14-mer and 10-mer) are progressively more specific in their targeting but also reduced in activity by nearly an order of magnitude. As shown in FIGS. 10C and 10D, 10-mer TALEs show near single-base mismatch resolution, losing almost all activity against targets bearing 2 mismatches (in the heat plot the target sequence positions are labeled from 1-10 starting from the 5' end). Taken together, these data imply that engineering shorter TALEs can yield higher specificity in genome engineering applications, while the requirement for FokI dimerization in TALE nuclease applications is essential to avoid off-target effect. See Kim et al., *Proceedings of the National Academy of Sciences of the United States of America* 93, 1156-1160 (1996) and Pattanayak et al., *Nature Methods* 8, 765-770 (2011) each of which are hereby incorporated by reference in its entirety.

Figure 8:
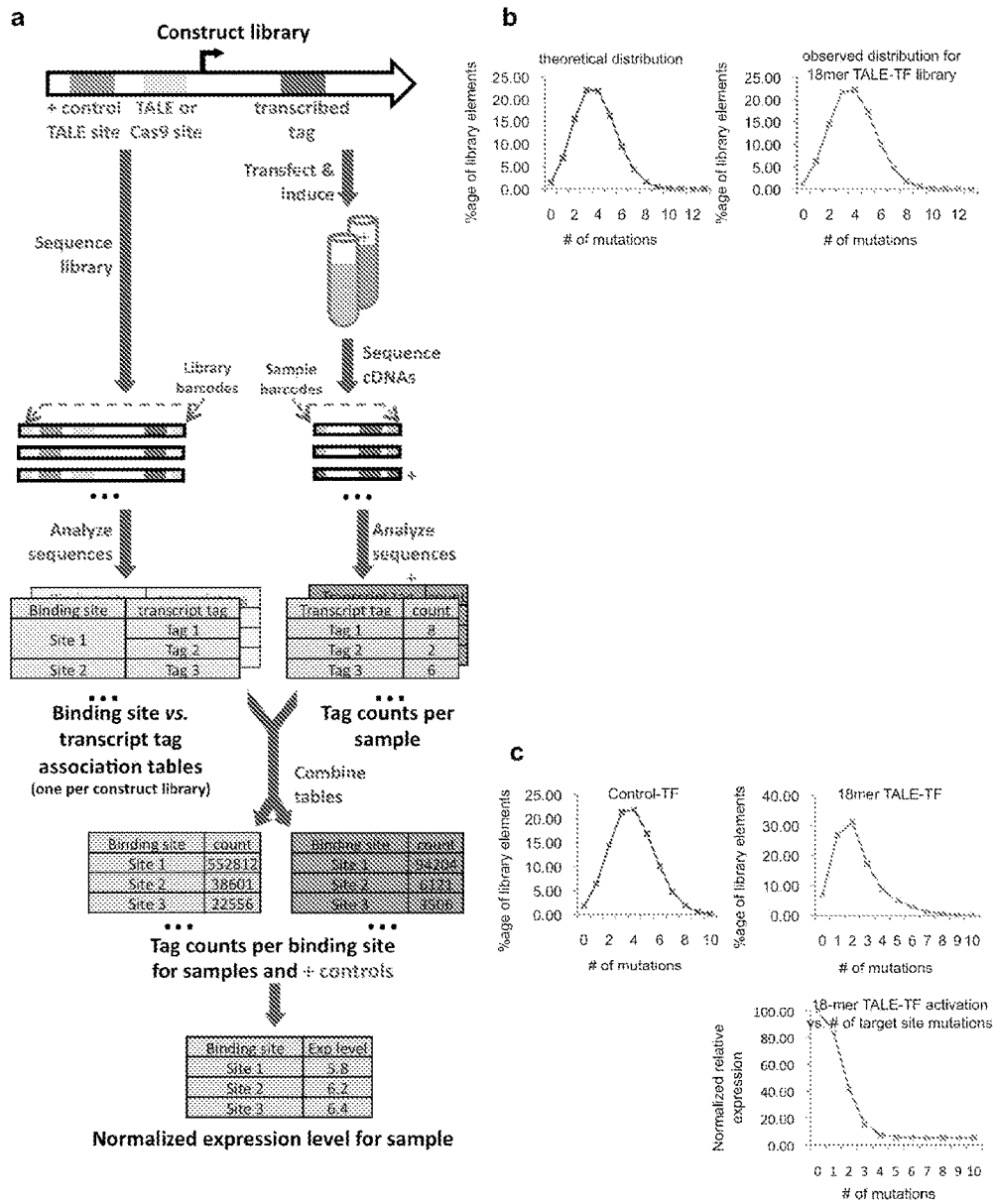
FIG. 8A depicts in schematic a high level specificity analysis processing flow for calculation of normalized expression levels.
FIG. 8B depicts data of distributions of percentages of binding sites by numbers of mismatches generated within a biased construct library. Left: Theoretical distribution. Right: Distribution observed from an actual TALE construct library.
FIG. 8C depicts data of distributions of percentages of tag counts aggregated to binding sites by numbers of mismatches. Left: Distribution observed from the positive control sample. Right: Distribution observed from a sample in which a non-control TALE was induced.

FIGS. 8A-8C are directed to high level specificity analysis processing flow for calculation of normalized expression levels illustrated with examples from experimental data. As shown in FIG. 8A, construct libraries are generated with a biased distribution of binding site sequences and random sequence 24 bp tags that will be incorporated into reporter gene transcripts (top). The transcribed tags are highly degenerate so that they should map many-to-one to Cas9 or TALE binding sequences. The construct libraries are sequenced ($3^{rd}$ level, left) to establish which tags co-occur with binding sites, resulting in an association table of binding sites vs. transcribed tags ($4^{th}$ level, left). Multiple construct libraries built for different binding sites may be sequenced at once using library barcodes (indicated here by the light blue and light yellow colors; levels 1-4, left). A construct library is then transfected into a cell population and a set of different Cas9/gRNA or TALE transcription factors are induced in samples of the populations ($2^{nd}$ level, right). One sample is always induced with a fixed TALE activator targeted to a fixed binding site sequence within the construct (top level, green box); this sample serves as a positive control (green sample, also indicated by a + sign). cDNAs generated from the reporter mRNA molecules in the induced samples are then sequenced and analyzed to obtain tag counts for each tag in a sample ($3^{rd}$ and $4^{th}$ level, right). As with the construct library sequencing, multiple samples, including the positive control, are sequenced and analyzed together by appending sample barcodes. Here the light red color indicates one non-control sample that has been sequenced and analyzed with the positive control (green). Because only the transcribed tags and not the construct binding sites appear in each read, the binding site vs. tag association table obtained from construct library sequencing is then used to tally up total counts of tags expressed from each binding site in each sample ($5^{th}$ level). The tallies for each non-positive control sample are then converted to normalized expression levels for each binding site by dividing them by the tallies obtained in the positive control sample. Examples of plots of normalized expression levels by numbers of mismatches are provided in FIGS. 2B and 2E, and in FIG. 9A and FIG. 10B. Not covered in this overall process flow are several levels of filtering for erroneous tags, for tags not associable with a construct library, and for tags apparently shared with multiple binding sites. FIG. 8B depicts example distributions of percentages of binding sites by numbers of mismatches generated within a biased construct library. Left: Theoretical distribution. Right: Distribution observed from an actual TALE construct library. FIG. 8C depicts example distributions of percentages of tag counts aggregated to binding sites by numbers of mismatches. Left: Distribution observed from the positive control sample. Right: Distribution observed from a sample in which a non-control TALE was induced. As the positive control TALE binds to a fixed site in the construct, the distribution of aggregated tag counts closely reflects the distribution of binding sites in FIG. 8B, while the distribution is skewed to the left for the non-control TALE sample because sites with fewer mismatches induce higher expression levels. Below: Computing the relative enrichment between these by dividing the tag counts obtained for the target-TF by those obtained for the control-TF reveals the average expression level versus the number of mutations in the target site.

Figure 9:
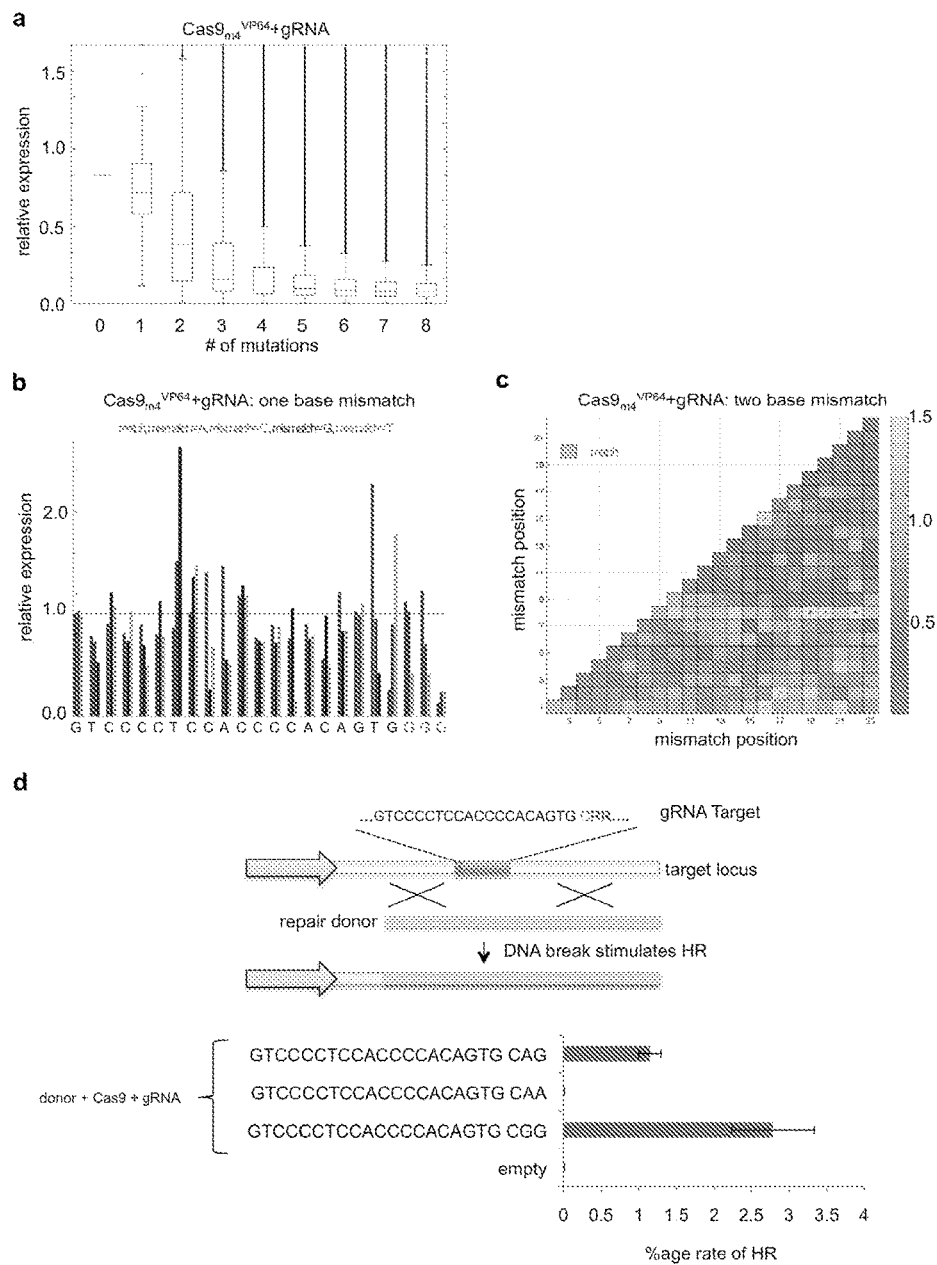
FIG. 9A depicts data for analysis of the targeting landscape of a Cas9-gRNA complex showing tolerance to 1-3 mutations in its target sequence.
FIG. 9B depicts data for analysis of the targeting landscape of a Cas9-gRNA complex showing insensitivity to point mutations, except those localized to the PAM sequence (SEQ ID NO: 2).
FIG. 9C depicts heat plot data for analysis of the targeting landscape of a Cas9-gRNA complex showing that introduction of 2 base mismatches significantly impairs activity.
FIG. 9D depicts data from a nuclease mediated HR assay confirming that the predicted PAM for the S. pyogenes Cas9 is NGG and also NAG.

These results are further reaffirmed by specificity data generated using a different Cas9-gRNA complex. As shown in FIG. 9A, a different Cas9-gRNA complex is tolerant to 1-3 mutations in its target sequence. As shown in FIG. 9B, the Cas9-gRNA complex is also largely insensitive to point mutations, except those localized to the PAM sequence. As shown in FIG. 9C, introduction of 2 base mismatches however significantly impairs activity (in the heat plot the target sequence positions are labeled from 1-23 starting from the 5' end). As shown in FIG. 9D, it was confirmed using a nuclease mediated HR assay that the predicted PAM for the *S. pyogenes* Cas9 is NGG and also NAG.

According to certain aspects, binding specificity is increased according to methods described herein. Because synergy between multiple complexes is a factor in target gene activation by Cas9N-VP64, transcriptional regulation applications of Cas9N is naturally quite specific as individual off-target binding events should have minimal effect. According to one aspect, off-set nicks are used in methods of genome-editing. A large majority of nicks seldom result in NHEJ events, (see Certo et al., *Nature Methods* 8, 671-676 (2011) hereby incorporated by reference in its entirety) thus minimizing the effects of off-target nicking. In contrast, inducing off-set nicks to generate double stranded breaks (DSBs) is highly effective at inducing gene disruption. According to certain aspects, 5' overhangs generate more significant NHEJ events as opposed to 3' overhangs. Similarly, 3' overhangs favor HR over NHEJ events, although the total number of HR events is significantly lower than when a 5' overhang is generated. Accordingly, methods are provided for using nicks for homologous recombination and off-set nicks for generating double stranded breaks to minimize the effects of off-target Cas9-gRNA activity.

Figure 3:
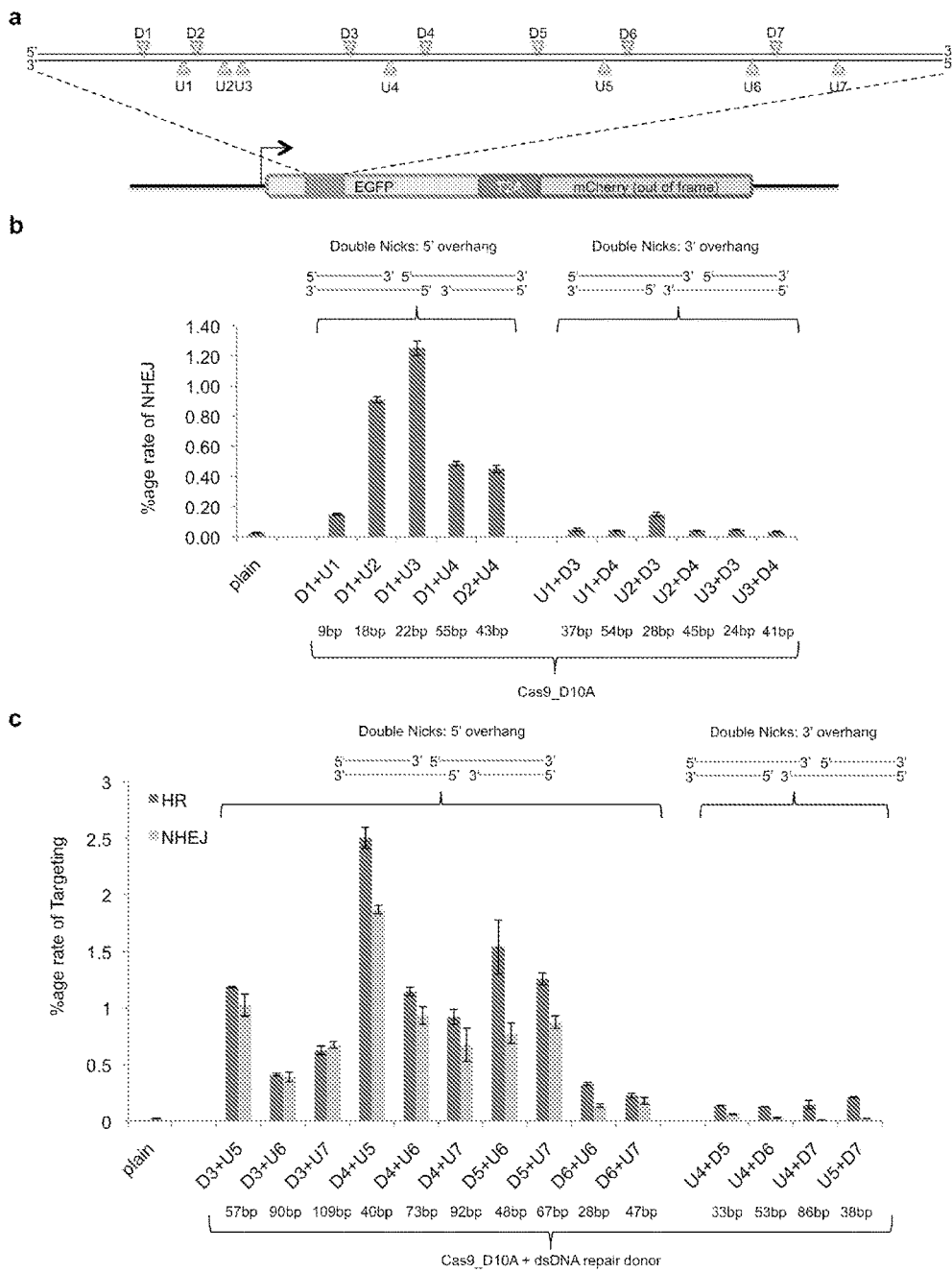
FIG. 3A depicts a schematic of a guide RNA design.
FIG. 3B depicts data showing percentage rate of non-homologous end joining for off-set nicks leading to 5' overhangs and off-set nicks leading to 5' overhangs.
FIG. 3C depicts data showing percentage rate of targeting for off-set nicks leading to 5' overhangs and off-set nicks leading to 5' overhangs.

FIGS. 3A-3C are directed to multiplex off-set nicking and methods for reducing the off-target binding with the guide RNAs. As shown in FIG. 3A, the traffic light reporter was used to simultaneously assay for HR and NHEJ events upon introduction of targeted nicks or breaks. DNA cleavage events resolved through the HDR pathway restore the GFP sequence, whereas mutagenic NHEJ causes frameshifts rendering the GFP out of frame and the downstream mCherry sequence in frame. For the assay, 14 gRNAs covering a 200 bp stretch of DNA: 7 targeting the sense strand (U1-7) and 7 the antisense strand (D1-7) were designed. Using the Cas9D10A mutant, which nicks the complementary strand, different two-way combinations of the gRNAs were used to induce a range of programmed 5' or 3' overhangs (the nicking sites for the 14 gRNAs are indicated). As shown in FIG. 3B, inducing off-set nicks to generate double stranded breaks (DSBs) is highly effective at inducing gene disruption. Notably off-set nicks leading to 5' overhangs result in more NHEJ events as opposed to 3' overhangs. As shown in FIG. 3C, generating 3' overhangs also favors the ratio of HR over NHEJ events, but the total number of HR events is significantly lower than when a 5' overhang is generated.

Figure 11:
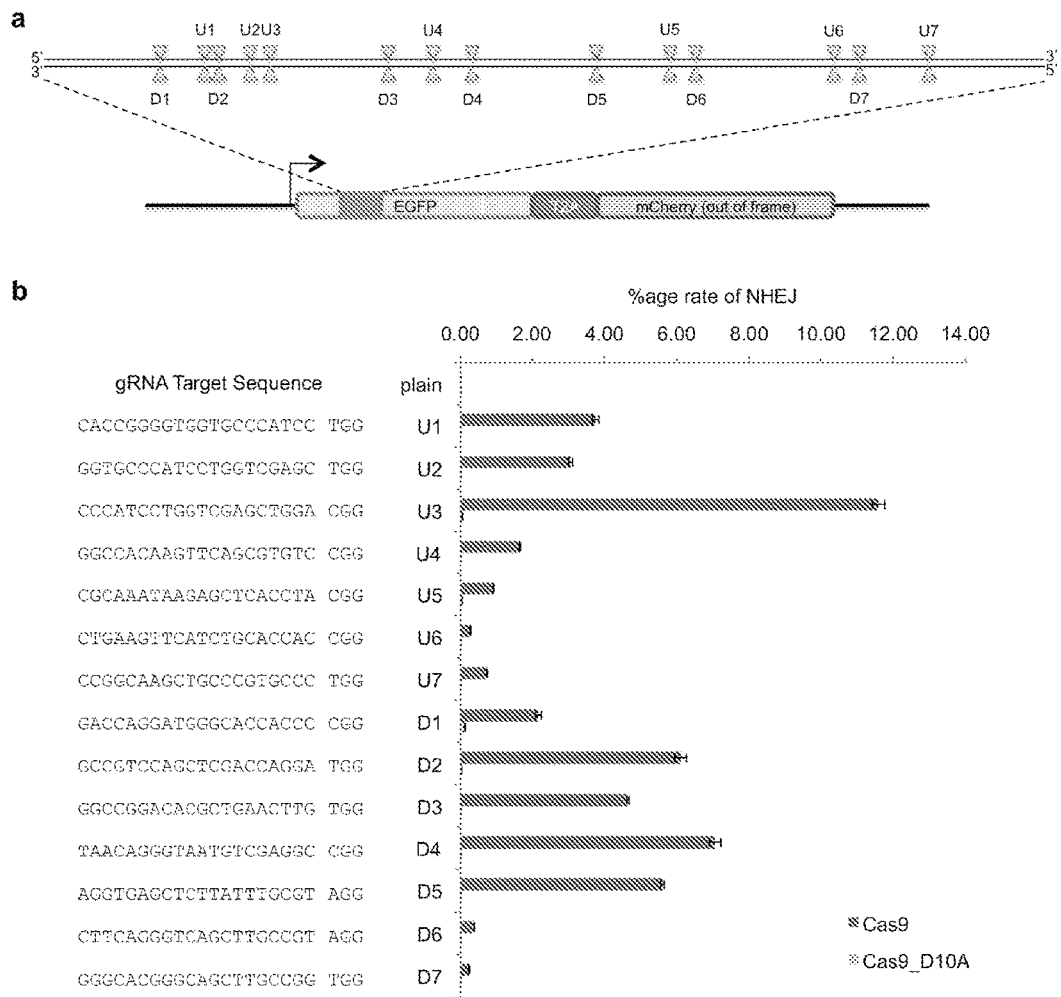
FIG. 11A depicts designed guide RNAs.
FIG. 11B depicts percentage rate of non-homologous end joining for various guide RNAs (SEQ ID NOS 17-30, respectively, in order of appearance).

FIGS. 11A-11B are directed to Cas9D10A nickase mediated NHEJ. As shown in FIG. 11A, the traffic light reporter was used to assay NHEJ events upon introduction of targeted nicks or double-stranded breaks. Briefly, upon introduction of DNA cleavage events, if the break goes through mutagenic NHEJ, the GFP is translated out of frame and the downstream mCherry sequences are rendered in frame resulting in red fluorescence. 14 gRNAs covering a 200 bp stretch of DNA: 7 targeting the sense strand (U1-7) and 7 the antisense strand (D1-7) were designed. As shown in FIG. 11B, it was observed that unlike the wild-type Cas9 which results in DSBs and robust NHEJ across all targets, most nicks (using the Cas9D10A mutant) seldom result in NHEJ events. All 14 sites are located within a contiguous 200 bp stretch of DNA and over 10-fold differences in targeting efficiencies were observed.

According to certain aspects, methods are described herein of modulating expression of a target nucleic acid in a cell that include introducing one or more, two or more or a plurality of foreign nucleic acids into the cell. The foreign nucleic acids introduced into the cell encode for a guide RNA or guide RNAs, a nuclease-null Cas9 protein or proteins and a transcriptional regulator protein or domain Together, a guide RNA, a nuclease-null Cas9 protein and a transcriptional regulator protein or domain are referred to as a co-localization complex as that term is understood by one of skill in the art to the extent that the guide RNA, the nuclease-null Cas9 protein and the transcriptional regulator protein or domain bind to DNA and regulate expression of a target nucleic acid. According to certain additional aspects, the foreign nucleic acids introduced into the cell encode for a guide RNA or guide RNAs and a Cas9 protein nickase. Together, a guide RNA and a Cas9 protein nickase are referred to as a co-localization complex as that term is understood by one of skill in the art to the extent that the guide RNA and the Cas9 protein nickase bind to DNA and nick a target nucleic acid.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, fungal cells, archael cells, eubacterial cells and the like. Cells include eukaryotic cells such as yeast cells, plant cells, and animal cells. Particular cells include mammalian cells. Further, cells include any in which it would be beneficial or desirable to regulate a target nucleic acid. Such cells may include those which are deficient in expression of a particular protein leading to a disease or detrimental condition. Such diseases or detrimental conditions are readily known to those of skill in the art. According to the present disclosure, the nucleic acid responsible for expressing the particular protein may be targeted by the methods described herein and a transcriptional activator resulting in upregulation of the target nucleic acid and corresponding expression of the particular protein. In this manner, the methods described herein provide therapeutic treatment.

Target nucleic acids include any nucleic acid sequence to which a co-localization complex as described herein can be useful to either regulate or nick. Target nucleic acids include genes. For purposes of the present disclosure, DNA, such as double stranded DNA, can include the target nucleic acid and a co-localization complex can bind to or otherwise co-localize with the DNA at or adjacent or near the target nucleic acid and in a manner in which the co-localization complex may have a desired effect on the target nucleic acid. Such target nucleic acids can include endogenous (or naturally occurring) nucleic acids and exogenous (or foreign) nucleic acids. One of skill based on the present disclosure will readily be able to identify or design guide RNAs and Cas9 proteins which co-localize to a DNA including a target nucleic acid. One of skill will further be able to identify transcriptional regulator proteins or domains which likewise co-localize to a DNA including a target nucleic acid. DNA includes genomic DNA, mitochondrial DNA, viral DNA or exogenous DNA.

Foreign nucleic acids (i.e. those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources.

Transcriptional regulator proteins or domains which are transcriptional activators include VP16 and VP64 and others readily identifiable by those skilled in the art based on the present disclosure.

Diseases and detrimental conditions are those characterized by abnormal loss of expression of a particular protein. Such diseases or detrimental conditions can be treated by upregulation of the particular protein. Accordingly, methods of treating a disease or detrimental condition are provided where the co-localization complex as described herein associates or otherwise binds to DNA including a target nucleic acid, and the transcriptional activator of the co-localization complex upregulates expression of the target nucleic acid. For example upregulating PRDM16 and other genes promoting brown fat differentiation and increased metabolic uptake can be used to treat metabolic syndrome or obesity. Activating anti-inflammatory genes are useful in autoimmunity and cardiovascular disease. Activating tumor suppressor genes is useful in treating cancer. One of skill in the art will readily identify such diseases and detrimental conditions based on the present disclosure.

The following examples are set forth as being representative of the present disclosure. These examples are not to be construed as limiting the scope of the present disclosure as these and other equivalent embodiments will be apparent in view of the present disclosure, figures and accompanying claims.

Example I

Cas9 Mutants

Sequences homologous to Cas9 with known structure were searched to identify candidate mutations in Cas9 that could ablate the natural activity of its RuvC and HNH domains. Using HHpred (world wide website toolkit.tuebingen.mpg.de/hhpred), the full sequence of Cas9 was queried against the full Protein Data Bank (January 2013). This search returned two different HNH endonucleases that had significant sequence homology to the HNH domain of Cas9; PacI and a putative endonuclease (PDB IDs: 3M7K and 4H9D respectively). These proteins were examined to find residues involved in magnesium ion coordination. The corresponding residues were then identified in the sequence alignment to Cas9. Two Mg-coordinating side-chains in each structure were identified that aligned to the same amino acid type in Cas9. They are 3M7K D92 and N113, and 4H9D D53 and N77. These residues corresponded to Cas9 D839 and N863. It was also reported that mutations of PacI residues D92 and N113 to alanine rendered the nuclease catalytically deficient. The Cas9 mutations D839A and N863A were made based on this analysis. Additionally, HHpred also predicts homology between Cas9 and the N-terminus of a *Thermus thermophilus* RuvC (PDB ID: 4EP4). This sequence alignment covers the previously reported mutation D10A which eliminates function of the RuvC domain in Cas9. To confirm this as an appropriate mutation, the metal binding residues were determined as before. In 4EP4, D7 helps to coordinate a magnesium ion. This position has sequence homology corresponding to Cas9 D10, confirming that this mutation helps remove metal binding, and thus catalytic activity from the Cas9 RuvC domain.

Example II

Plasmid Construction

The Cas9 mutants were generated using the Quikchange kit (Agilent technologies). The target gRNA expression constructs were either (1) directly ordered as individual gBlocks from IDT and cloned into the pCR-BluntII-TOPO vector (Invitrogen); or (2) custom synthesized by Genewiz; or (3) assembled using Gibson assembly of oligonucleotides into the gRNA cloning vector (plasmid #41824). The vectors for the HR reporter assay involving a broken GFP were constructed by fusion PCR assembly of the GFP sequence bearing the stop codon and appropriate fragment assembled into the EGIP lentivector from Addgene (plasmid #26777). These lentivectors were then used to establish the GFP reporter stable lines. TALENs used in this study were constructed using standard protocols. See Sanjana et al., *Nature Protocols* 7, 171-192 (2012) hereby incorporated by reference in its entirety. Cas9N and MS2 VP64 fusions were performed using standard PCR fusion protocol procedures. The promoter luciferase constructs for OCT4 and REX1 were obtained from Addgene (plasmid #17221 and plasmid #17222).

Example III

Cell Culture and Transfections

HEK 293T cells were cultured in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). Cells were maintained at 37° C. and 5% $CO_2$ in a humidified incubator.

Transfections involving nuclease assays were as follows: $0.4 \times 10^6$ cells were transfected with 2 μg Cas9 plasmid, 2 μg gRNA and/or 2 μg DNA donor plasmid using Lipofectamine 2000 as per the manufacturer's protocols. Cells were harvested 3 days after transfection and either analyzed by FACS, or for direct assay of genomic cuts the genomic DNA of ~$1 \times 10^6$ cells was extracted using DNAeasy kit (Qiagen). For these PCR was conducted to amplify the targeting region with genomic DNA derived from the cells and amplicons were deep sequenced by MiSeq Personal Sequencer (Illumina) with coverage >200,000 reads. The sequencing data was analyzed to estimate NHEJ efficiencies.

For transfections involving transcriptional activation assays: $0.4 \times 10^6$ cells were transfected with (1) 2 μg Cas9N-VP64 plasmid, 2 μg gRNA and/or 0.25 μg of reporter construct; or (2) 2 μg Cas9N plasmid, 2 μg MS2-VP64, 2 μg gRNA-2XMS2aptamer and/or 0.25 μg of reporter construct. Cells were harvested 24-48 hrs post transfection and assayed using FACS or immunofluorescence methods, or their total RNA was extracted and these were subsequently analyzed by RT-PCR. Here standard taqman probes from Invitrogen for OCT4 and REX1 were used, with normalization for each sample performed against GAPDH.

For transfections involving transcriptional activation assays for specificity profile of Cas9-gRNA complexes and TALEs: $0.4 \times 10^6$ cells were transfected with (1) 2 μg Cas9N-VP64 plasmid, 2 μg gRNA and 0.25 μg of reporter library; or (2) 2 μg TALE-TF plasmid and 0.25m of reporter library; or (3) 2 μg control-TF plasmid and 0.25 μg of reporter library. Cells were harvested 24 hrs post transfection (to avoid the stimulation of reporters being in saturation mode). Total RNA extraction was performed using RNAeasy-plus kit (Qiagen), and standard RT-per performed using Superscript-III (Invitrogen). Libraries for next-generation sequencing were generated by targeted per amplification of the transcript-tags.

Example IV

Computational and Sequence Analysis for Calculation of Cas9-TF and TALE-TF Reporter Expression Levels The high-level logic flow for this process is depicted in FIG. 8A, and additional details are given here. For details on construct library composition, see FIGS. 8A (level 1) and 8B.

Sequencing:
For Cas9 experiments, construct library (FIG. 8A, level 3, left) and reporter gene cDNA sequences (FIG. 8A, level 3, right) were obtained as 150 bp overlapping paired end reads on an Illumina MiSeq, while for TALE experiments, corresponding sequences were obtained as 51 bp non-overlapping paired end reads on an Illumina HiSeq.

Construct Library Sequence Processing:
Alignment: For Cas9 experiments, novoalign V2.07.17 (world wide website novocraft.com/main/index/php) was used to align paired reads to a set of 250 bp reference sequences that corresponded to 234 bp of the constructs flanked by the pairs of 8 bp library barcodes (see FIG. 8A, $3^{rd}$ level, left). In the reference sequences supplied to novoalign, the 23 bp degenerate Cas9 binding site regions and the 24 bp degenerate transcript tag regions (see FIG. 8A, first level) were specified as Ns, while the construct library barcodes were explicitly provided. For TALE experiments, the same procedures were used except that the reference sequences were 203 bp in length and the degenerate binding site regions were 18 bp vs. 23 bp in length. Validity checking: Novoalign output for comprised files in which left and right reads for each read pair were individually aligned to the reference sequences. Only read pairs that were both uniquely aligned to the reference sequence were subjected to additional validity conditions, and only read pairs that passed all of these conditions were retained. The validity conditions included: (i) Each of the two construct library barcodes must align in at least 4 positions to a reference sequence barcode, and the two barcodes must to the barcode pair for the same construct library. (ii) All bases aligning to the N regions of the reference sequence must be called by novoalign as As, Cs, Gs or Ts. Note that for neither Cas9 nor TALE experiments did left and right reads overlap in a reference N region, so that the possibility of ambiguous novoalign calls of these N bases did not arise. (iii) Likewise, no novoalign-called inserts or deletions must appear in these regions. (iv) No Ts must appear in the transcript tag region (as these random sequences were generated from As, Cs, and Gs only). Read pairs for which any one of these conditions were violated were collected in a rejected read pair file. These validity checks were implemented using custom perl scripts.

Induced Sample Reporter Gene cDNA Sequence Processing:
Alignment: SeqPrep (downloaded from world wide website github.com/jstjohn/SeqPrep) was first used to merge the overlapping read pairs to the 79 bp common segment, after which novoalign (version above) was used to align these 79 bp common segments as unpaired single reads to a set of reference sequences (see FIG. 8A, $3^{rd}$ level, right) in which (as for the construct library sequencing) the 24 bp degenerate transcript tag was specified as Ns while the sample barcodes were explicitly provided. Both TALE and Cas9 cDNA sequence regions corresponded to the same 63 bp regions of cDNA flanked by pairs of 8 bp sample barcode sequences. Validity checking: The same conditions were applied as for construct library sequencing (see above) except that: (a) Here, due prior SeqPrep merging of read pairs, validity processing did not have to filter for unique alignments of both reads in a read pair but only for unique alignments of the merged reads. (b) Only transcript tags appeared in the cDNA sequence reads, so that validity processing only applied these tag regions of the reference sequences and not also to a separate binding site region.

Assembly of Table of Binding Sites Vs. Transcript Tag Associations:
Custom perl was used to generate these tables from the validated construct library sequences (FIG. 8A, $4^{th}$ level, left). Although the 24 bp tag sequences composed of A, C, and G bases should be essentially unique across a construct library (probability of sharing=~2.8e−11), early analysis of binding site vs. tag associations revealed that a non-negligible fraction of tag sequences were in fact shared by multiple binding sequences, likely mainly caused by a combination of sequence errors in the binding sequences, or oligo synthesis errors in the oligos used to generate the construct libraries. In addition to tag sharing, tags found associated with binding sites in validated read pairs might also be found in the construct library read pair reject file if it was not clear, due to barcode mismatches, which construct library they might be from. Finally, the tag sequences themselves might contain sequence errors. To deal with these sources of error, tags were categorized with three attributes: (i) safe vs. unsafe, where unsafe meant the tag could be found in the construct library rejected read pair file; shared vs. nonshared, where shared meant the tag was found associated with multiple binding site sequences, and 2+ vs. 1-only, where 2+ meant that the tag appeared at least twice among the validated construct library sequences and so presumed to be less likely to contain sequence errors. Combining these three criteria yielded 8 classes of tags associated with each binding site, the most secure (but least abundant) class comprising only safe, nonshared, 2+ tags; and the least secure (but most abundant) class comprising all tags regardless of safety, sharing, or number of occurrences. Computation of Normalized Expression Levels:

Custom perl code was used to implement the steps indicated in FIG. 8A, levels 5-6. First, tag counts obtained for each induced sample were aggregated for each binding site, using the binding site vs. transcript tag table previously computed for the construct library (see FIG. 8C). For each sample, the aggregated tag counts for each binding site were then divided by the aggregated tag counts for the positive control sample to generate normalized expression levels. Additional considerations relevant to these calculations included:

1. For each sample, a subset of "novel" tags were found among the validity-checked cDNA gene sequences that could not be found in the binding site vs. transcript tag association table. These tags were ignored in the subsequent calculations.

2. The aggregations of tag counts described above were performed for each of the eight classes of tags described above in binding site vs. transcript tag association table. Because the binding sites in the construct libraries were biased to generate sequences similar to a central sequence frequently, but sequences with increasing numbers of mismatches increasingly rarely, binding sites with few mismatches generally aggregated to large numbers of tags, while binding sites with more mismatches aggregated to smaller numbers. Thus, although use of the most secure tag class was generally desirable, evaluation of binding sites with two or more mismatches might be based on small numbers of tags per binding site, making the secure counts and ratios less statistically reliable even if the tags themselves were more reliable. In such cases, all tags were used. Some compensation for this consideration obtains from the fact that the number of separate aggregated tag counts for n mismatching positions grew with the number of combinations of mismatching positions (equal to $$\binom{L}{n} 3^n),$$

and so dramatically increases with n; thus the averages of aggregated tag counts for different numbers n of mismatches (shown in FIGS. 2B, 2E, and in FIGS. 9A, 10B) are based on a statistically very large set of aggregated tag counts for n≥2.

3. Finally, the binding site built into the TALE construct libraries was 18 bp and tag associations were assigned based on these 18 bp sequences, but some experiments were conducted with TALEs programmed to bind central 14 bp or 10 bp regions within the 18 bp construct binding site regions. In computing expression levels for these TALEs, tags were aggregated to binding sites based on the corresponding regions of the 18 bp binding sites in the association table, so that binding site mismatches outside of this region were ignored.

Example V

Vector and Strain Construction

Cas9 sequences from *S. thermophilus*, *N. meningitidis*, and *T. denticola* were obtained from NCBI and human codon optimized using JCAT (world wide website jcat.de)[27] and modified to facilitate DNA synthesis and expression in *E. coli*. 500 bp gBlocks (Integrated DNA Technologies, Coralville Iowa) were joined by hierarchical overlap PCR and isothermal assembly[24]. The resulting full-length products were subcloned into bacterial and human expression vectors. Nuclease-null Cas9 cassettes (NM: D16A D587A H588A N611A, SP: D10A D839A H840A N863A, ST1: D9A D598A H599A N622A, TD: D13A D878A H879A N902A) were constructed from these templates by standard methods.

Example VI

Bacterial Plasmids

Cas9 was expressed in bacteria from a cloDF13/aadA plasmid backbone using the medium-strength proC constitutive promoter. tracrRNA cassettes, including promoters and terminators from the native bacterial loci, were synthesized as gBlocks and inserted downstream of the Cas9 coding sequence for each vector for robust tracrRNA production. When the tracrRNA cassette was expected to additionally contain a promoter in the opposite orientation, the lambda t1 terminator was inserted to prevent interference with cas9 transcription. Bacterial targeting plasmids were based on a p15A/cat backbone with the strong J23100 promoter followed by one of two 20 base pair spacer sequences (FIG. 13D) previously determined to function using SP. Spacer sequences were immediately followed by one of the three 36 base pair repeat sequences depicted in FIG. 12A. The YFP reporter vector was based on a pSC101/kan backbone with the pR promoter driving GFP and the T7 g10 RBS preceding the EYFP coding sequence, with protospacer 1 and AAAAGATT PAM inserted into the non-template strand in the 5' UTR. Substrate plasmids for orthogonality testing in bacteria were identical to library plasmids (see below) but with the following PAMs: GAAGGGTT (NM), GGGAGGTT (SP), GAAGAATT (ST1), AAAAAGGG (TD).

Example VII

Mammalian Vectors

Mammalian Cas9 expression vectors were based on pcDNA3.3-TOPO with C-terminal SV40 NLSs. sgRNAs for each Cas9 were designed by aligning crRNA repeats with tracrRNAs and fusing the 5' crRNA repeat to the 3' tracrRNA so as to leave a stable stem for Cas9 interaction[25]. sgRNA expression constructs were generated by cloning 455 bp gBlocks into the pCR-BluntII-TOPO vector backbone. Spacers were identical to those used in previous work[8]. Lentivectors for the broken-GFP HR reporter assay were modified from those previously described to include appropriate PAM sequences for each Cas9 and used to establish the stable GFP reporter lines.

RNA-guided transcriptional activators consisted of nuclease-null Cas9 proteins fused to the VP64 activator and corresponding reporter constucts bearing a tdTomato driven by a minimal promoter were constructed.

Example VIII

Library Construction and Transformation

Protospacer libraries were constructed by amplifying the pZE21 vector (ExpressSys, Ruelzheim, Germany) using primers (IDT, Coralville, Iowa) encoding one of the two protospacer sequences followed by 8 random bases and assembled by standard isothermal methods[24]. Library assemblies were initially transformed into NEBTurbo cells (New England Biolabs, Ipswich Mass.), yielding >1E8 clones per library according to dilution plating, and purified by Midiprep (Qiagen, Carlsbad Calif.). Electrocompetent NEBTurbo cells containing a Cas9 expression plasmid (DS-NMcas, DS-ST1cas, or DS-TDcas) and a targeting plasmid (PM-NM!sp1, PM-NM!sp2, PM-ST1!sp1, PM-ST1 !sp2, PM-TD!sp1, or PM-TD!sp2) were transformed with 200 ng of each library and recovered for 2 hours at 37° C. prior to dilution with media containing spectinomycin (50 μg/mL), chloramphenicol (30 μg/mL), and kanamycin (50 μg/mL). Serial dilutions were plated to estimate post-transformation library size. All libraries exceeded ~1E7 clones, indicative of complete coverage of the 65,536 random PAM sequences.

Example IX

High-Throughput Sequencing

Library DNA was harvested by spin columns (Qiagen, Carlsbad Calif.) after 12 hours of antibiotic selection. Intact PAMs were amplified with barcoded primers and sequences obtained from overlapping 25 bp paired-end reads on an Illumina MiSeq. MiSeq yielded 18,411,704 total reads or 9,205,852 paired-end reads with an average quality score >34 for each library. Paired end reads were merged and filtered for perfect alignment to each other, their protospacer, and the plasmid backbone. The remaining 7,652,454 merged filtered reads were trimmed to remove plasmid backbone and protospacer sequences, then used to generate position weight matrices for each PAM library. Each library combination received at least 450,000 high-quality reads.

Example X

Sequence Processing

To calculate the fold depletion for each candidate PAM, we employed two scripts to filter the data. patternProp (usage: python patternProp.py [PAM] file.fastq) returns the number and fraction of reads matching each 1-base derivative of the indicated PAM. patternProp3 returns the fraction of reads matching each 1-base derivative relative to the total number of reads for the library. Spreadsheets detailing depletion ratios for each calculated PAM were used to identify the minimal fold depletion among all 1-base derivatives and thereby classify PAMs.

Example XI

Repression and Orthogonality Assays in Bacteria

Cas9-mediated repression was assayed by transforming the NM expression plasmid and the YFP reporter plasmid with each of the two corresponding targeting plasmids. Colonies with matching or mismatched spacer and protospacer were picked and grown in 96-well plates. Fluorescence at 495/528 nm and absorbance at 600 nm were measured using a Synergy Neo microplate reader (BioTek, Winooski Vt.).

Orthogonality tests were performed by preparing electrocompetent NEBTurbo cells bearing all combinations of Cas9 and targeting plasmids and transforming them with matched or mismatched substrate plasmids bearing appropriate PAMs for each Cas9. Sufficient cells and dilutions were plated to ensure that at least some colonies appeared even for correct Cas9+targeting+matching protospacer combinations, which typically arise due to mutational inactivation of the Cas9 or the crRNA. Colonies were counted and fold depletion calculated for each.

Example XII

Cell Culture and Transfections

HEK 293T cells were cultured in Dulbecco's modified Eagle's medium (DMEM, Invitrogen) high glucose supplemented with 10% fetal bovine serum (FBS, Invitrogen), penicillin/streptomycin (pen/strep, Invitrogen), and non-essential amino acids (NEAA, Invitrogen). Cells were maintained at 37° C. and 5% $CO_2$ in a humidified incubator.

Transfections involving nuclease assays were as follows: $0.4 \times 10^6$ cells were transfected with 2 μg Cas9 plasmid, 2 μg gRNA and/or 2 μg DNA donor plasmid using Lipofectamine 2000 as per the manufacturer's protocols. Cells were harvested 3 days after transfection and either analyzed by FACS, or for direct assay of genomic cuts the genomic DNA of ~$1 \times 10^6$ cells was extracted using DNAeasy kit (Qiagen).

For transfections involving transcriptional activation assays: $0.4 \times 10^6$ cells were transfected with 2 μg $Cas9_N$-VP64 plasmid, 2 μg gRNA and/or 0.25 μg of reporter construct. Cells were harvested 24-48 hrs post transfection and assayed using FACS or immunofluorescence methods, or their total RNA was extracted and these were subsequently analyzed by RT-PCR.

Example XIII

Selecting Putatively Orthogonal Cas9 Proteins

Figure 12:
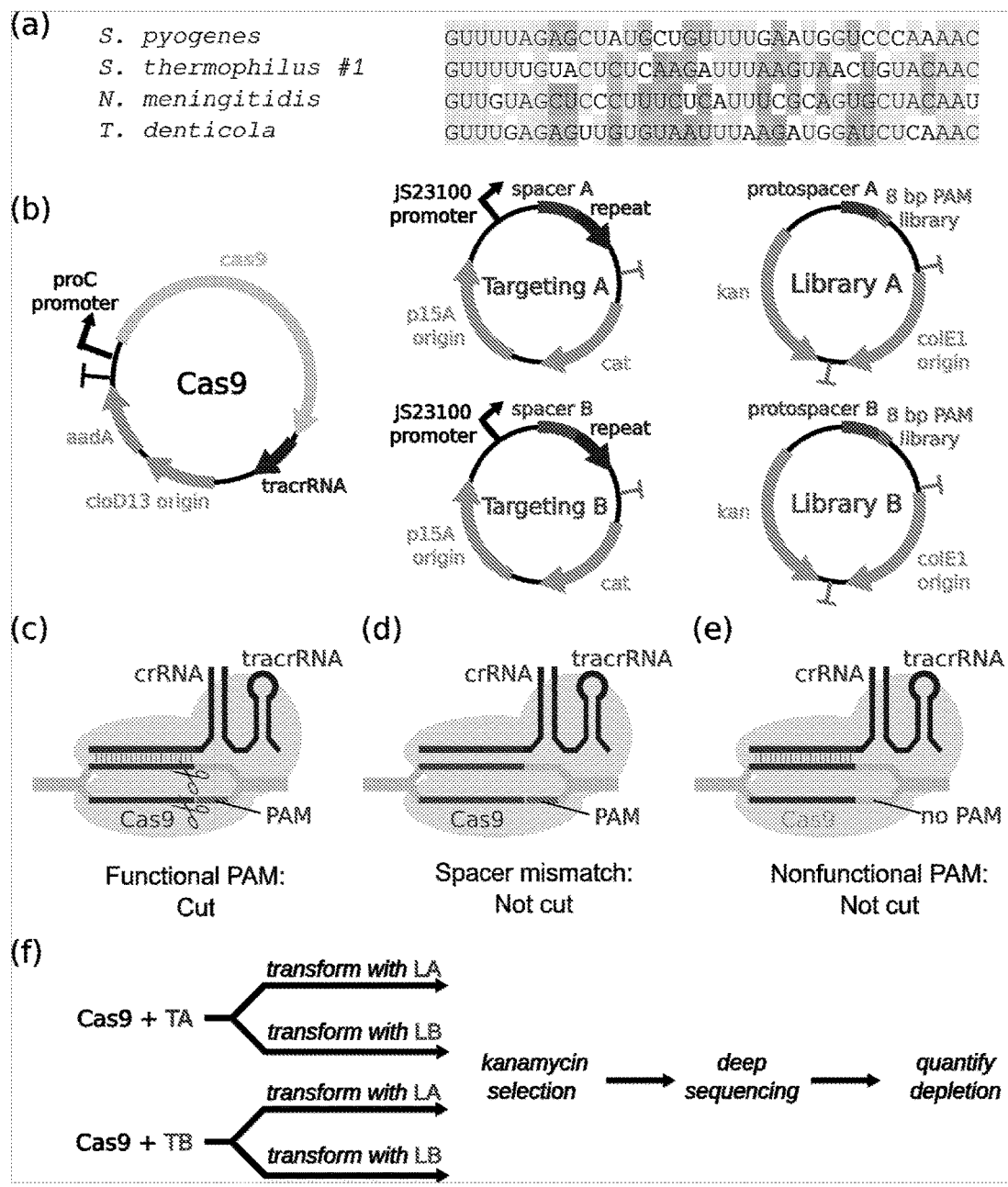
FIGS. 12A-12F depict comparison and characterization of putatively orthogonal Cas9 proteins.

Cas9 RNA binding and sgRNA specificity is primarily determined by the 36 base pair repeat sequence in crRNA. Known Cas9 genes were examined for highly divergent repeats in their adjacent CRISPR loci. *Streptococcus pyogenes* and *Streptococcus thermophilus* CRISPR1 Cas9 proteins (SP and ST1)[6, 22] and two additional Cas9 proteins from *Neisseria meningitidis* (NM) and *Treponema denticola* (TD) were selected whose loci harbor repeats that differ by at least 13 nucleotides from one another and from those of SP and ST1 (FIG. 12A).

Example XIV

PAM Characterization

Cas9 proteins will only target dsDNA sequences flanked by a 3' PAM sequence specific to the Cas9 of interest. Of the four Cas9 variants, only SP has an experimentally characterized PAM, while the ST1 PAM and, very recently, the NM PAM were deduced bioinformatically. SP is readily targetable due to its short PAM of NGG[10], while ST1 and NM targeting are less radily targetable because of PAMs of NNAGAAW and NNNNGATT, respectively[22, 23]. Bioinformatic approaches inferred more stringent PAM requirements for Cas9 activity than are empirically necessary for effector cleavage due to the spacer acquisition step. Because the PAM sequence is the most frequent target of mutation in escape phages, redundancy in the acquired PAM would preclude resistance. A library-based approach was adopted to comprehensively characterize these sequences in bacteria using high-throughput sequencing.

Genes encoding ST1, NM, and TD were assembled from synthetic fragments and cloned into bacterial expression plasmids along with their associated tracrRNAs (FIG. 12B). Two SP-functional spacers were selected for incorporation into the six targeting plasmids. Each targeting plasmid encodes a constitutively expressed crRNA in which one of the two spacers is followed by the 36 base-pair repeat sequence specific to a Cas9 protein (FIG. 12B). Plasmid libraries containing one of the two protospacers followed by all possible 8 base pair PAM sequences were generated by PCR and assembly[24]. Each library was electroporated into E. coli cells harboring Cas9 expression and targeting plasmids, for a total of 12 combinations of Cas9 protein, spacer, and protospacer. Surviving library plasmids were selectively amplified by barcoded PCR and sequenced by MiSeq to distinguish between functional PAM sequences, which are depleted only when the spacer and protospacer match (FIG. 12C-12D), from nonfunctional PAMs, which are never depleted (FIG. 12D-12E). To graphically depict the importance of each nucleotide at every position, the log relative frequency of each base for matched spacer-protospacer pairs relative to the corresponding mismatched case was plotted (FIGS. 13A-13F).

Figure 13:
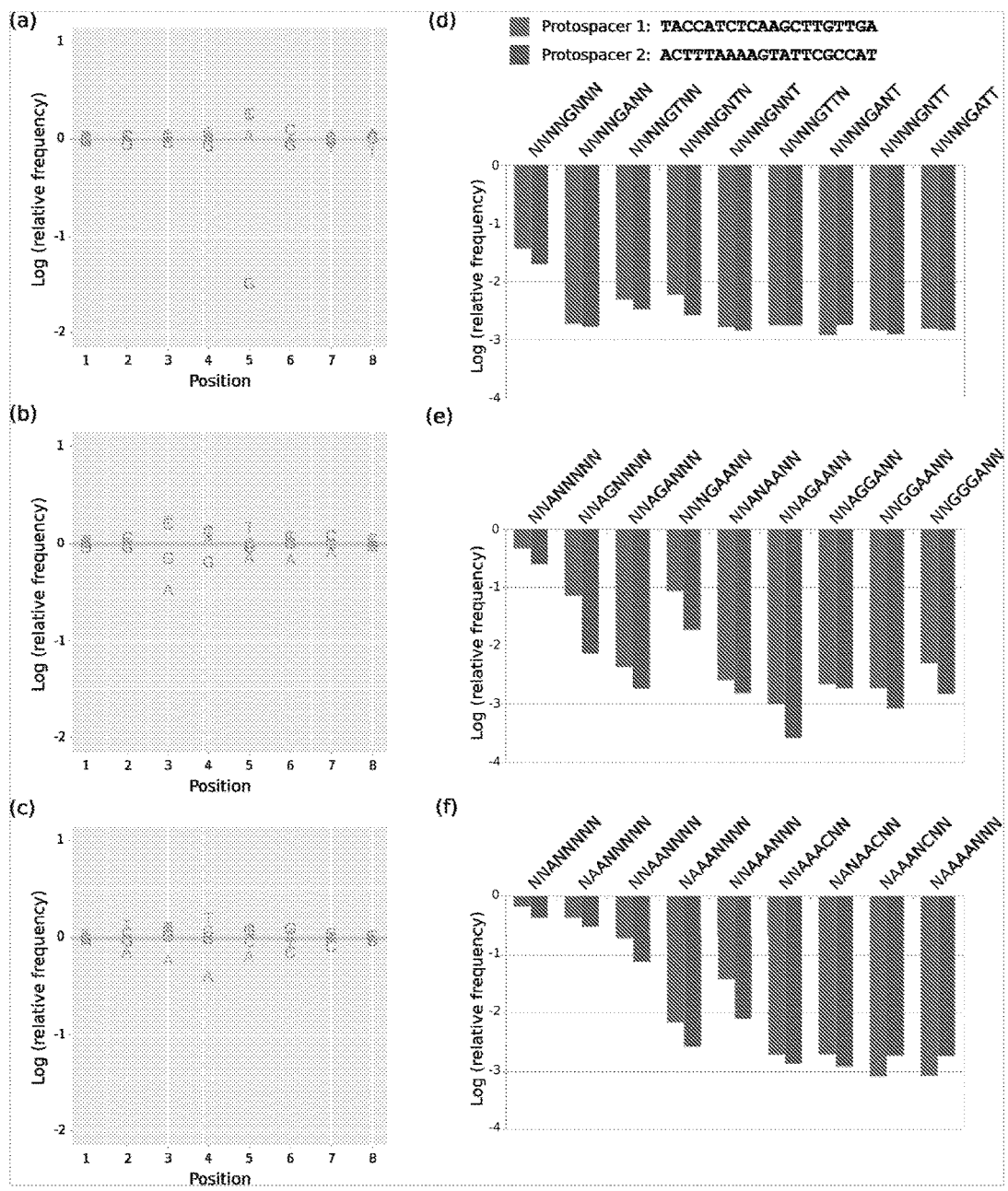
FIGS. 13A-13F depict depletion of functional protospacer-adjacent motifs (PAMs) from libraries by Cas9 proteins. The log frequency of each base at every position for matched spacer-protospacer pairs is plotted relative to control conditions in which spacer and protospacer do not match. Results reflect the mean depletion of libraries by NM (FIG. 13A), ST1 (FIG. 13B), and TD (FIG. 13C) based on two distinct protospacer sequences (SEQ ID NOS 35 and 36, respectively, in order of appearance) (FIG. 13D). Depletion of specific sequences for each protospacer are plotted separately for each Cas9 protein (FIG. 13E-13F).

NM and ST1 recognize PAMs that are less stringent and more complex than earlier bioinformatic predictions, suggesting that requirements for spacer acquisition are more stringent than those for effector cleavage. NM primarily requires a single G nucleotide positioned five bases from the 3' end of the protospacer (FIG. 13A), while ST1 and TD each require at least three specific bases (FIG. 5b-c). Sorting results by position allowed quantification of depletion of any PAM sequence from each protospacer library (FIGS. 13D-13F). All three enzymes cleaved protospacer 2 more effectively than protospacer 1 for nearly all PAMs, with ST1 exhibiting an approximately 10-fold disparity. However, there was also considerable PAM-dependent variation in this interaction. For example, NM cleaved protospacers 1 and 2 approximately equally when they were followed by sequences matching TNNNGNNN, but was 10-fold more active in cleaving protospacer 2 when the PAMs matched ANNNGNNN.

Results highlight the difficulty of defining a single acceptable PAM for a given Cas9. Not only do activity levels depend on the protospacer sequence, but specific combinations of unfavorable PAM bases can significantly reduce activity even when the primary base requirements are met. We initially identified PAMs as patterns that underwent >100-fold average depletion with the lower-activity protospacer 1 and >50-fold depletion of all derivatives with one additional base fixed (Table 1, plain text). While these levels are presumably sufficient to defend against targets in bacteria, particular combinations of deleterious mutations dramatically reduced activity. For example, NM depleted sequences matching NCCAGGTN by only 4-fold. A more stringent threshold requiring >500-fold depletion of matching sequences and >200-fold depletion of one-base derivatives was defined for applications requiring high affinity (Table 1, bolded).

TABLE 1

| NM | ST1 | TD |
|---|---|---|
| NNNNGANN | NNAGAA | NAAAAN |
| NNNNGTTN | NNAGGA | NAAANC |
| NNNNGNNT | NNGGAA | NANAAC |
| NNNNGTNN | NNANAA | NNAAAC |
| NNNNGNTN | NNGGGA | |

Example XV

Transcriptional Regulation in Bacteria

Figure 14:
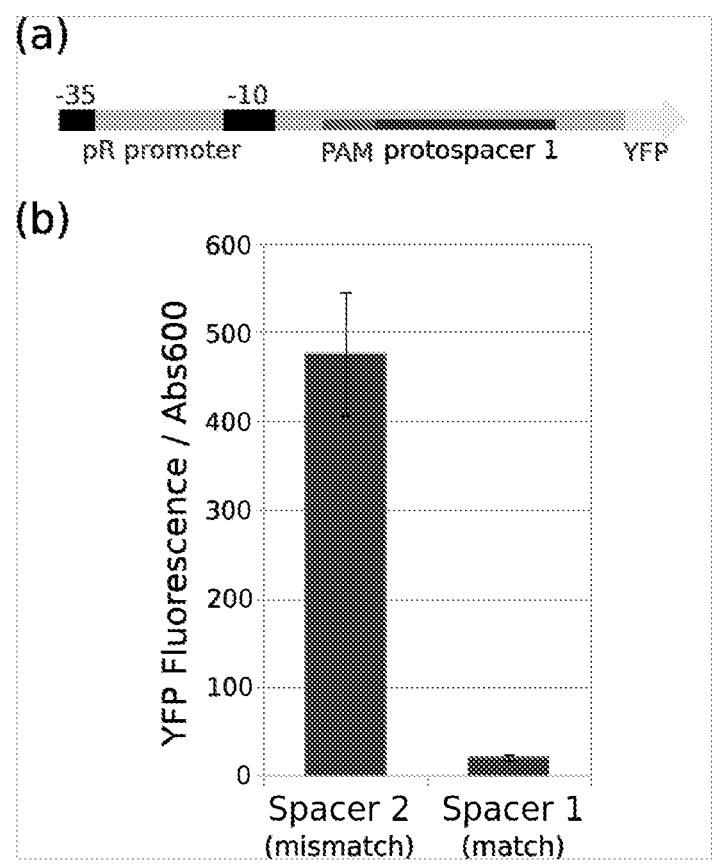
FIGS. 14A-14B depict transcriptional repression mediated by NM.

A nuclease-null variant of SP has been demonstrated to repress targeted genes in bacteria with an efficacy dependent upon the position of the targeted protospacer and PAM[18]. Because the PAM of NM occurs more frequently than that of SP, nuclease-null version may be similarly capable of targeted repression. The catalytic residues of the RuvC and HNH nuclease domains were identified by sequence homology and inactivated to generate a putative nuclease-null NM. To create a suitable reporter, protospacer 1 was inserted with an appropriate PAM into the non-template strand within the 5'UTR of a YFP reporter plasmid (FIG. 14A). These constructs were cotransformed into E. coli together with each of the two NM targeting plasmids used previously and measured their comparative fluorescence. Cells with matching spacer and protospacer exhibited ~22-fold weaker fluorescence than the corresponding mismatched case (FIG. 14B). These results suggest that NM can function as an easily targeted repressor to control transcription in bacteria, substantially increasing the number of endogenous genes that can be subjected to Cas9-mediated repression.

Example XVI

Orthogonality in Bacteria

Figure 15:
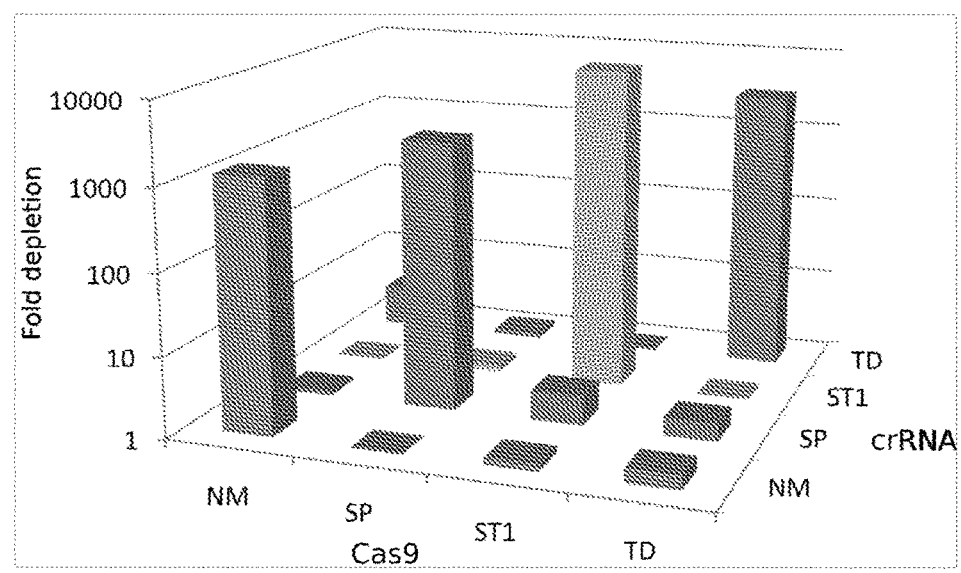
FIG. 15 depicts orthogonal recognition of crRNAs in E. coli. Cells with all combinations of Cas9 and crRNA were challenged with a plasmid bearing a matched or mismatched protospacer and appropriate PAM. Sufficient cells were plated to reliably obtain colonies from matching spacer and protospacer pairings and total colony counts used to calculate the fold depletion.

A set of Cas9 proteins were selected for their disparate crRNA repeat sequences. To verify that they are in fact orthogonal, each Cas9 expression plasmid was co-transformed with all four targeting plasmids containing spacer 2. These cells were challenged by transformation of substrate plasmids containing either protospacer 1 or protospacer 2 and a suitable PAM. Plasmid depletion was observed exclusively when each Cas9 was paired with its own crRNA, demonstrating that all four constructs are indeed orthogonal in bacteria (FIG. 15).

Example XVII

Genome Editing in Human Cells

Figure 16:
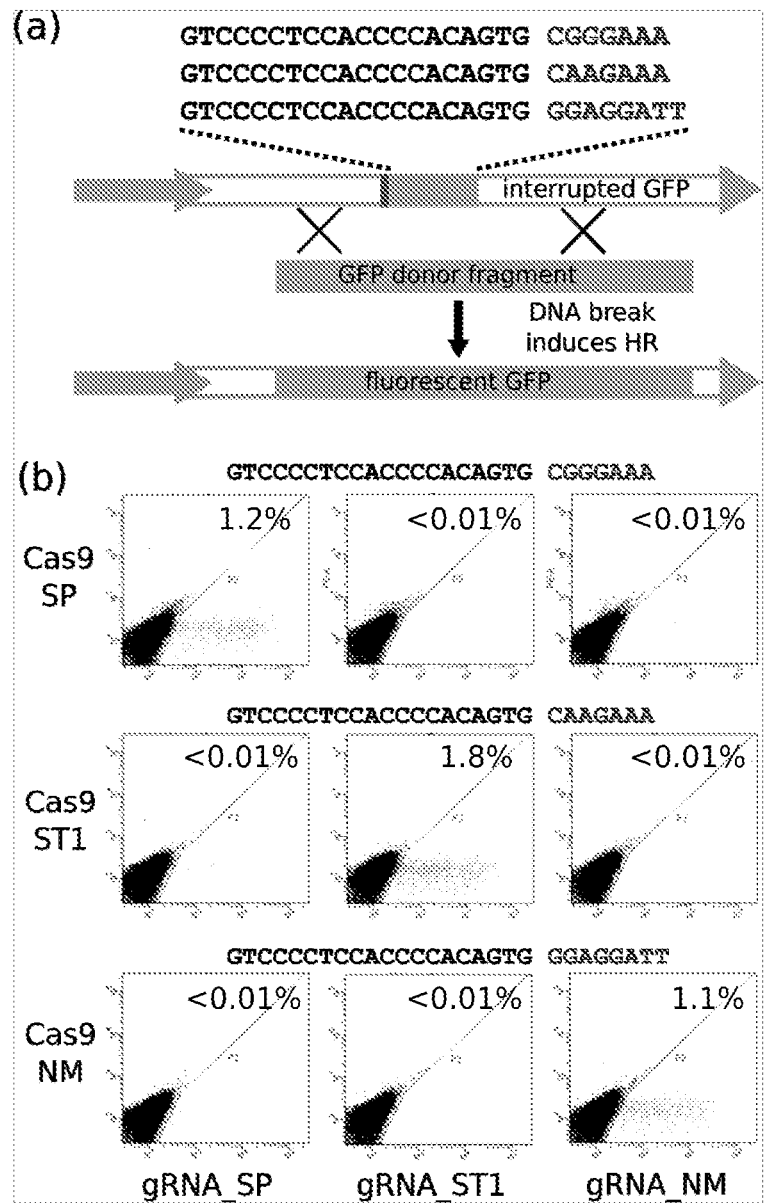
FIGS. 16A-16B depict Cas9-mediated gene editing in human cells.

These Cas9 variants were then used to engineer human cells. Single guide RNAs (sgRNAs) were constructed from the corresponding crRNAs and tracrRNAs for NM and ST1, the two smaller Cas9 orthologs, by examining complementary regions between crRNA and tracrRNA[25] and fusing the two sequences via a stem-loop at various fusion junctions analogous to those of the sgRNAs created for SP. In certain instances where multiple successive uracils caused Pol III termination in the expression system, multiple single-base mutants were generated. The complete 3' tracrRNA sequence was always included, as truncations are known to be detrimental[8]. All sgRNAs were assayed for activity along with their corresponding Cas9 protein using a previously described homologous recombination assay in 293 cells[8]. Briefly, a genomically integrated non-fluorescent GFP reporter line was constructed for each Cas9 protein in which the GFP coding sequence was interrupted by an insert encoding a stop codon and protospacer sequence with functional PAM. Reporter lines were transfected with expression vectors encoding a Cas9 protein and corresponding sgRNA along with a repair donor capable of restoring fluorescence upon nuclease-induced homologous recombination (FIG. 16A). ST1- and NM-mediated editing was observed at levels comparable to those induced by SP. The ST1 sgRNA with 5 successive uracils functioned efficiently, suggesting that Pol III termination did not occur at levels sufficient to impair activity. Full-length crRNA-tracrRNA fusions were active in all instances and are useful for chimeric sgRNA design. Both NM and ST1 are capable of efficient gene editing in human cells using chimeric guide RNAs.

Example XVIII

Cas9 Orthogonality in Mammalian Cells

Having discovered highly effective sgRNAs for NM and ST1 activity in human cells, it was verified that none of the three proteins can be guided by the sgRNAs of the others. The same homologous recombination assay was used to measure the comparative efficiency of NM, SP, and ST1 in combination with each of the three sgRNAs. All three Cas9 proteins were determined to be fully orthogonal to one another, demonstrating that they are capable of targeting distinct and non-overlapping sets of sequences within the same cell (FIG. 16B). To contrast the roles of sgRNA and PAM in orthogonal targeting, a variety of downstream PAM sequences with SP and ST1 and their respective sgRNAs were tested. Both a matching sgRNA and a valid PAM are required for activity, with the orthogonality determined almost entirely by the specific sgRNA affinity for the corresponding Cas9.

Example XIX

Transcriptional Activation in Human Cells

Figure 17:
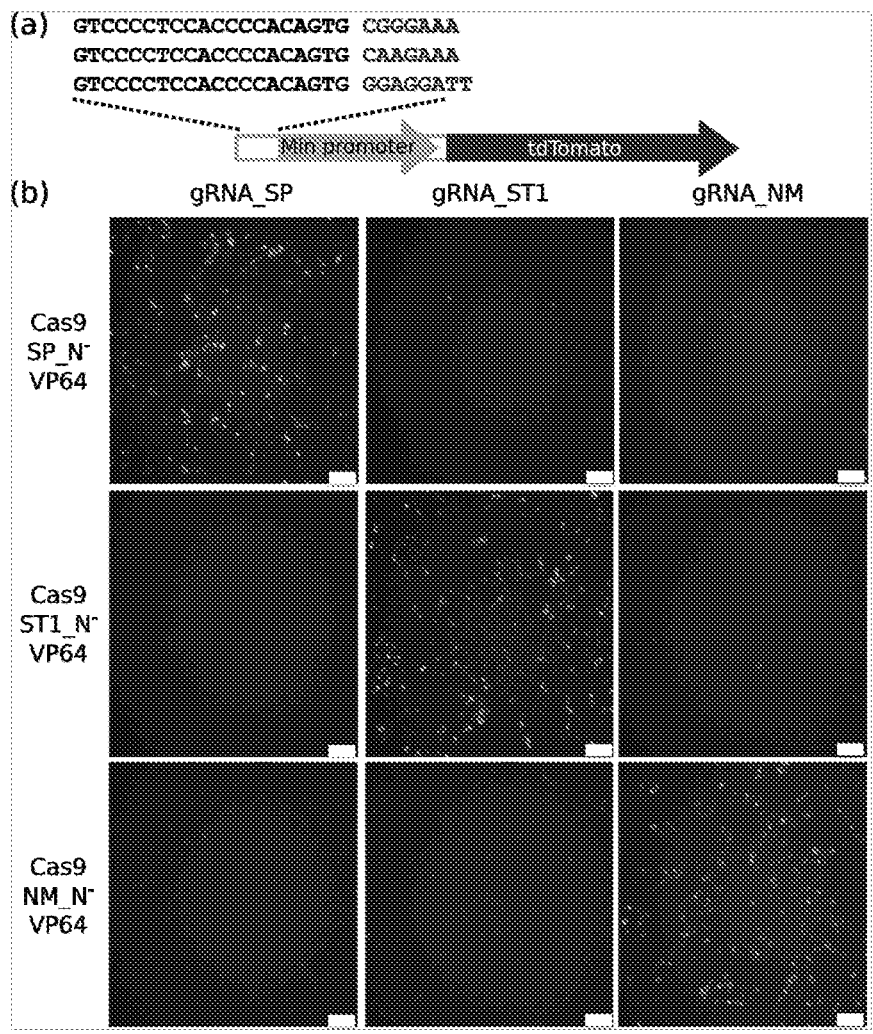
FIGS. 17A-17B depict transcriptional activation in human cells.

NM and ST1 mediate transcriptional activation in human cells. Nuclease-null NM and ST1 genes were fused to the VP64 activator domain at their C-termini to yield putative RNA-guided activators modeled after the SP activator. Reporter constructs for activation consisted of a protospacer with an appropriate PAM inserted upstream of the tdTomato coding region. Vectors expressing an RNA-guided transcriptional activator, an sgRNA, and an appropriate reporter were cotransfected and the extent of transcriptional activation measured by FACS (FIG. 17A). In each case, robust transcriptional activation by all three Cas9 variants was observed (FIG. 17B). Each Cas9 activator stimulated transcription only when paired with its corresponding sgRNA.

Example XX

Discussion

Using two distinct protospacers for comprehensive PAM characterization allowed investigation of the complexities governing protospacer and PAM recognition. Differential protospacer cleavage efficiencies exhibited a consistent trend across diverse Cas9 proteins, although the magnitude of the disparity varied considerably between orthologs. This pattern suggests that sequence-dependent differences in D-loop formation or stabilization determine the basal targeting efficiency for each protospacer, but that additional Cas9 or repeat-dependent factors also play a role. Similarly, numerous factors preclude efforts to describe PAM recognition with a single sequence motif. Individual bases adjacent to the primary PAM recognition determinants can combine to dramatically decrease overall affinity. Indeed, certain PAMs appear to interact nonlinearly with the spacer or protospacer to determine the overall activity. Moreover, different affinity levels may be required for distinct activities across disparate cell types. Finally, experimentally identified PAMs required fewer bases than those inferred from bioinformatic analyses, suggesting that spacer acquisition requirements differ from those for effector cleavage.

This difference is most significant for the Cas9 protein from *Neisseria meningitidis*, which has fewer PAM requirements relative to both its bioinformatic prediction and to the currently popular Cas9 from *S. pyogenes*. Its discovery considerably expands the number of sequences that can be readily targeted with a Cas9 protein. At 3.25 kbp in length, it is also 850 bp smaller than SP, a significant advantage when gene delivery capabilities are limiting. Most notably, both NM and ST1 are small enough to fit into an AAV vector for therapeutic applications, while NM may represent a more suitable starting point for directed evolution efforts designed to alter PAM recognition or specificity.

The following references are hereby incorporated by reference in their entireties for all purposes.

REFERENCES

1. Bhaya, D., Davison, M. & Barrangou, R. CRISPR-Cas systems in bacteria and archaea: versatile small RNAs for adaptive defense and regulation. *Annual review of genetics* 45, 273-297 (2011).
2. Wiedenheft, B., Sternberg, S. H. & Doudna, J. A. RNA-guided genetic silencing systems in bacteria and archaea. *Nature* 482, 331-338 (2012).
3. Gasiunas, G., Barrangou, R., Horvath, P. & Siksnys, V. Cas9-crRNA ribonucleoprotein complex mediates specific DNA cleavage for adaptive immunity in bacteria. *Proceedings of the National Academy of Sciences of the United States of America* 109, E2579-2586 (2012).
4. Jinek, M. et al. A programmable dual-RNA-guided DNA endonuclease in adaptive bacterial immunity. *Science* 337, 816-821 (2012).
5. Cho, S. W., Kim, S, Kim, J M & Kim, J S Targeted genome engineering in human cells with the Cas9 RNA-guided endonuclease. *Nature biotechnology* 31, 230-232 (2013).
6. Cong, L. et al. Multiplex genome engineering using CRISPR/Cas systems. *Science* 339, 819-823 (2013).
7. Ding, Q. et al. Enhanced efficiency of human pluripotent stem cell genome editing through replacing TALENs with CRISPRs. *Cell stem cell* 12, 393-394 (2013).
8. Mali, P. et al. RNA-guided human genome engineering via Cas9. *Science* 339, 823-826 (2013).
9. Wang, H. et al. One-Step Generation of Mice Carrying Mutations in Multiple Genes by CRISPR/Cas-Mediated Genome Engineering. *Cell* 153, 910-918 (2013).

10. Jiang, W., Bikard, D., Cox, D., Zhang, F. & Marraffini, L. A. RNA-guided editing of bacterial genomes using CRISPR-Cas systems. *Nature biotechnology* 31, 233-239 (2013).
11. Boch, J. et al. Breaking the code of DNA binding specificity of TAL-type III effectors. *Science* 326, 1509-1512 (2009).
12. Gaj, T., Gersbach, C. A. & Barbas, C. F., 3rd ZFN, TALEN, and CRISPR/Cas-based methods for genome engineering. *Trends in biotechnology* (2013).
13. Hockemeyer, D. et al. Efficient targeting of expressed and silent genes in human ESCs and iPSCs using zinc-finger nucleases. *Nature biotechnology* 27, 851-857 (2009).
14. Kim, Y.G., Cha, J. & Chandrasegaran, S. Hybrid restriction enzymes: zinc finger fusions to Fok I cleavage domain. *Proceedings of the National Academy of Sciences of the United States of America* 93, 1156-1160 (1996).
15. Moscou, M. J. & Bogdanove, A. J. A simple cipher governs DNA recognition by TAL effectors. *Science* 326, 1501 (2009).
16. Porteus, M. H. & Carroll, D. Gene targeting using zinc finger nucleases. *Nature biotechnology* 23, 967-973 (2005).
17. Urnov, F. D. et al. Highly efficient endogenous human gene correction using designed zinc-finger nucleases. *Nature* 435, 646-651 (2005).
18. Qi, L. S. et al. Repurposing CRISPR as an RNA-guided platform for sequence-specific control of gene expression. *Cell* 152, 1173-1183 (2013).
19. Beerli, R. R., Dreier, B. & Barbas, C. F., 3rd Positive and negative regulation of endogenous genes by designed transcription factors. *Proceedings of the National Academy of Sciences of the United States of America* 97, 1495-1500 (2000).
20. Podgornaia, A. I. & Laub, M. T. Determinants of specificity in two-component signal transduction. *Current opinion in microbiology* 16, 156-162 (2013).
21. Purnick, P. E. & Weiss, R. The second wave of synthetic biology: from modules to systems. *Nature reviews. Molecular cell biology* 10, 410-422 (2009).
22. Horvath, P. et al. Diversity, activity, and evolution of CRISPR loci in *Streptococcus thermophilus*. *Journal of bacteriology* 190, 1401-1412 (2008).
23. Zhang, Y. et al. Processing-Independent CRISPR RNAs Limit Natural Transformation in *Neisseria meningitidis*. *Molecular cell* 50, 488-503 (2013).
24. Gibson, D. G. et al. Enzymatic assembly of DNA molecules up to several hundred kilobases. *Nature methods* 6, 343-345 (2009).
25. Deltcheva, E. et al. CRISPR RNA maturation by trans-encoded small RNA and host factor RNase III. *Nature* 471, 602-607 (2011).
26. Bondy-Denomy, J., Pawluk, A., Maxwell, K. L. & Davidson, A. R. Bacteriophage genes that inactivate the CRISPR/Cas bacterial immune system. *Nature* 493, 429-432 (2013).
27. Grote, A. et al. JCat: a novel tool to adapt codon usage of a target gene to its potential expression host. *Nucleic acids research* 33, W526-531 (2005).

The invention claimed is:

1. A cell in culture comprising
a first foreign nucleic acid encoding two or more guide RNAs complementary to two or more respective target nucleic acids,
a second foreign nucleic acid encoding two or more orthogonal RNA guided nuclease null DNA binding proteins, wherein each of the two or more orthogonal RNA guided nuclease null DNA binding proteins is of a different species and recognizes a corresponding PAM sequence in a target nucleic acid, and
a third foreign nucleic acid encoding two or more transcriptional regulator proteins, wherein the cell is configured to express the two or more guide RNAs, the two or more orthogonal RNA guided nuclease-null DNA binding proteins, and the two or more transcriptional regulator proteins, wherein the cell comprises two or more co-localization complexes with each including a guide RNA, an orthogonal RNA guided nuclease null DNA binding protein, a transcriptional regulator protein and a target nucleic acid.

2. The cell of claim 1 wherein the two or more transcriptional regulator proteins are each fused to an orthogonal RNA guided nuclease null DNA binding protein.

3. The cell of claim 1 wherein the first foreign nucleic acid encoding the two or more guide RNAs further encodes two or more targets of an RNA-binding domain and the third foreign nucleic acid encoding the two or more transcriptional regulator proteins further encodes two or more RNA-binding domains each fused to a transcriptional regulator protein.

4. The cell of claim 1 wherein the cell is a eukaryotic cell.

5. The cell of claim 1 wherein the cell is a yeast cell, a plant cell or an animal cell.

6. The cell of claim 1 wherein each guide RNA includes between about 10 to about 500 nucleotides.

7. The cell of claim 1 wherein each guide RNA includes between about 20 to about 100 nucleotides.

8. The cell of claim 1 wherein a transcriptional regulator protein is a transcriptional activator comprising VP16 or VP64.

9. The cell of claim 1 wherein each of the two or more transcriptional regulator proteins is a transcriptional repressor or activator.

10. The cell of claim 1 wherein each of the two or more guide RNAs is a tracrRNA-crRNA fusion.

11. The cell of claim 1 wherein the target nucleic acid is genomic DNA, mitochondrial DNA, viral DNA, or exogenous DNA.

12. The cell of claim 1 wherein a first target nucleic acid is activated and a second target nucleic acid is repressed.

13. The cell of claim 1 wherein a first plurality of target nucleic acids are activated and a second plurality of target nucleic acids are repressed.

14. The cell of claim 1 wherein a first one or more target nucleic acids are activated and a second one or more target nucleic acids are repressed.

15. The cell of claim 1 wherein each of the two or more RNA guided nuclease null DNA binding proteins is a DNA binding protein of a Type II CRISPR system.

16. The cell of claim 1 wherein each of the two or more RNA guided nuclease null DNA binding proteins is an orthogonal nuclease-null Cas9 protein.

17. The cell of claim 1 wherein each of the two or more orthogonal RNA guided nuclease-null DNA binding proteins binds to a corresponding species specific guide RNA bearing matching crRNA and tracrRNA sequences.

* * * * *